United States Patent [19]
Treco et al.

[11] Patent Number: 5,580,734
[45] Date of Patent: Dec. 3, 1996

[54] METHOD OF PRODUCING A PHYSICAL MAP CONTIGOUS DNA SEQUENCES

[75] Inventors: Douglas A. Treco, Arlington; Allan M. Miller, Medford, both of Mass.

[73] Assignee: Transkaryotic Therapies, Inc., Cambridge, Mass.

[21] Appl. No.: 301,872

[22] Filed: Sep. 6, 1994

Related U.S. Application Data

[63] Continuation of Ser. No. 739,861, Aug. 2, 1991, abandoned, which is a continuation-in-part of Ser. No. 552,183, Jul. 13, 1990, abandoned.

[51] Int. Cl.$^6$ .............................. C12Q 1/68; C12N 15/09
[52] U.S. Cl. .............................................. 435/6; 435/172.3
[58] Field of Search ....................................... 435/6, 172.3

[56] References Cited

PUBLICATIONS

Pavan et al. "Generation of deletion derivatives by targeted transformation of human–derived yeast artificial chromosomes", Proc. Natl. Acad. Sci. USA 87: 1300–1304. Feb. 1990.

Orr–Weaver et al. "Yeast transformation: a model system for the study of recombination", Proc. Natl. Acad. Sci. USA 78: 6345–6358. 1981.

Ma et al. "Plasmid construction by homologous recombination in yeast", Gene 58: 201–216. 1987.

Traver et al. "Rapid screening of a human genomic library in yeast artificial chromosomes for single –copy sequences", Proc. Natl. Acad. Sci. USA 86: 5898–5902. Aug. 1989.

Pavan et al. "Modification and transfer into an embryonal carcinoma cell line of a 360–kilobase human–derived yeast artificial chromosome", Mol. Cell. Biol. 10: 4163–4169. 1990.

Compton et al. "Insertion of nonhomologous DNA into the yeast genome mediated by homologous recombination with a cotransforming plasmid", Mol. Gen. Genet. 188:44–50. 1982.

Struhl et al. "High–frequency transformation of yeast: autonomos replication of hybrid DNA molecules", Proc. Natl. Acad. Sci. USA 76: 1035–1039. 1979.

Rothstein "Targeting, disruption, replacement, and allele rescue: Integrative DNA transformation in yeast" in Guthrie et al. (eds.), Methods in Enzymology, vol. 194, Academic Press, New York, pp. 281–301. 1991.

Vijayakumar et al. (1986) Structure of a conjugative element in Streptococcus pneumoniae. J. Bacteriol. 166: 978–984.

Stiles et al. (1981) DNA sequence of a mutation in the leader region of the yeast Iso–1–cytochrome c mRNA Cell 25:277–284.

Grimm et al. (1988) Observations on integrative transformation in Schizosaccharomyces pombe. Mol Gen Genet 215: 87–93.

Robins et al. (1981) Transforming DNA integrates into the host chromosome Cell 23: 29–39.

*Primary Examiner*—Mindy Fleisher
*Assistant Examiner*—Scott David Priebe
*Attorney, Agent, or Firm*—Hamilton, Brook, Smith & Reynolds, P.C.

[57] ABSTRACT

Materials and methods for homologous-recombination screening of DNA libraries constructed in a eukaryotic host and methods for homologous-recombination chromosome walking for isolating overlapping DNA sequences for building an extended physical map of a chromosomal region.

4 Claims, 17 Drawing Sheets

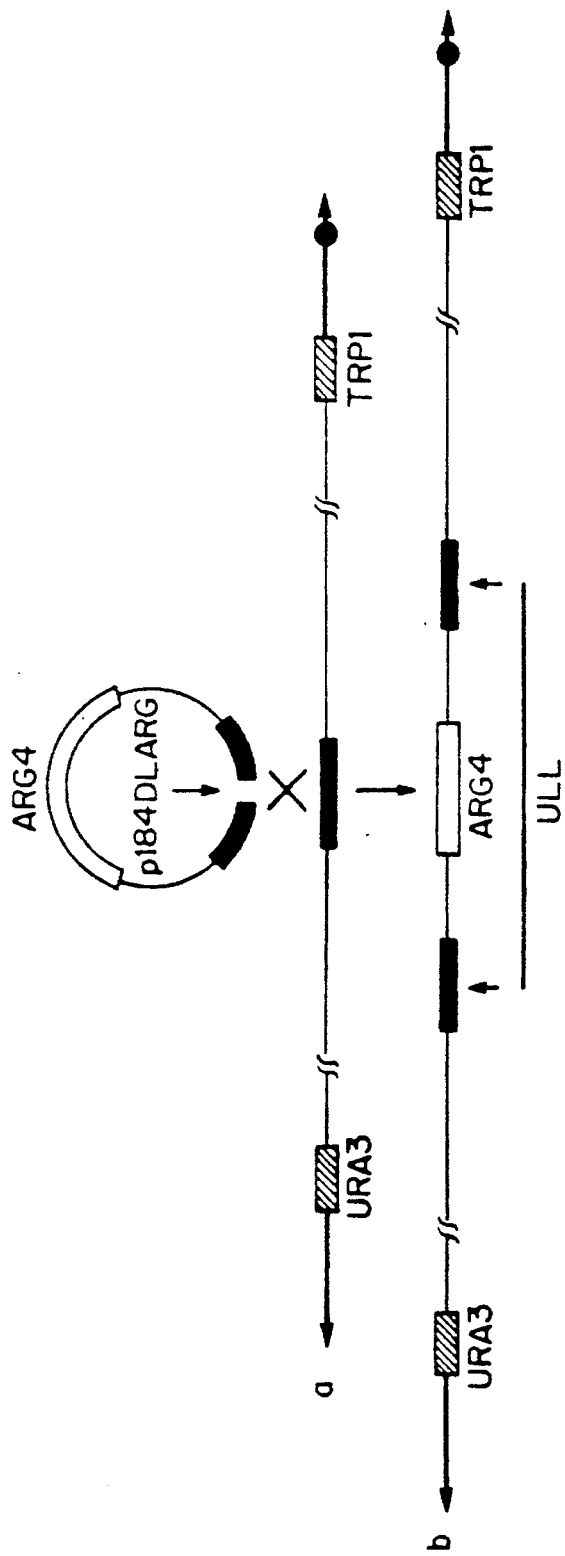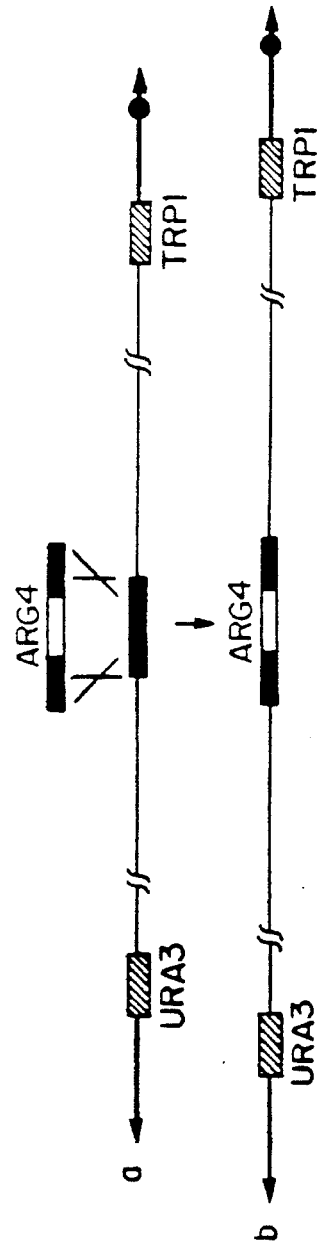
FIG. 2
FIG. 3 oligonucleotide

1    AATTCAACAA GCAAGTGCGA TGC

2    GATCCCGGGC CCATGCATCG CACTTGC

SmaI
     AATTCAACAAGCAAGTGCGATGCatgggcccgggatc
     ttaagttgttcgttcacgctacgtACCCGGGCCCTAG
                             NsiI  ApaI

3    AATTCACATG TGTCAACTAA ACATAAAACT CGAGGGGATC C

4    GATCTTTTAT AGGGCCCATG CATTACGTAG GATCCCCTCG AG

AATTCACATGTGTCAACTAAACATAAAACTCGAGGGGATCCtacgtaatgcatggccctataaaagatc
ttaagtgtacacagttgatttgtatttgagctCCCCTAGGATGCATTACGTACCCGGGATATTTTCTAG
     HincII                      XhoI  BamHI SnaBI NsiI  ApaI
                                       XhoII FIGURE 8a Oligonucleotide

5   AATTCGGATC TTTAAACATA AAAGCTTCCG GATCCCG

6   GATCATGCAT GGGCCCCGGGA TCCGGAAGC

SmaI
   AATTCGGATCTTTAAACATAAAAGCTTCCGGATCCCGggcccatgcatgatc
   ttaagcctagaaatttgtattttcGAAGGCCTAGGGCCCGGGTACGTACTAG
      XhoIIAhaIII    HindIII BamHI    ApaI NsiI
                             XhoII

7   GATCCTTTAA ACATAAAAGC TTGGAGATCT AG

8   CTAGGATGCA TGGGCCCAGT ACTAGATCTC CAAG

GATCCTTTAAACATAAAAGCTTGGAGATCTAGtactgggcccatgcatcctag
   ctaggaaatttgtattttcGAACCTCTAGATCATGACCCGGGTACCTAGGATC
           AhaIII   HindIII BglII ScaI ApaI NsiI
                               XhoII

9A  GATCTGAGCT CAAGGAACAG CTG

9B  CAGCTGTTCC TTGAGCTCA

GATCTGAGCTCAAGGAACAGCTG
      ACTCGAGTTCCTTGTCGAC
        SacI       PvuII

FIGURE 8b

Oligonucleotide

12    GGTCTCTACA GGTTCTGACA TTATT

13    CCGGCGTAGA GAATCCACAG GACGG

14    CTCCTGATGA CGCATGGTTA CTC

15    GGAAAGAAAT GCACAAGCTT TTGCC

16    CCGATACCAG GACCTTGCCA TCC

FIGURE 8c 5,580,734

METHOD OF PRODUCING A PHYSICAL MAP CONTIGOUS DNA SEQUENCES

RELATED APPLICATION

This application is a continuation of application Ser. No. 07/739,861 filed Aug. 2, 1991, now abandoned, which is a Continuation-in-Part of Ser. No. 07/552,183 filed Jul. 13, 1990, now abandoned.

BACKGROUND OF THE INVENTION

A genomic DNA "library" is formed by digesting genomic DNA from a particular organism with a suitable restriction enzyme, joining the genomic DNA fragments to vectors and introducing the DNA fragment-containing vectors into a population of host cells. Complementary DNA (cDNA) is DNA which has been produced by an enzyme known as reverse transcriptase which can synthesize a complementary strand of DNA (cDNA) using a mRNA strand as a template. A cDNA library is formed by joining the cDNA fragments to vectors and introducing the cDNA fragment-containing vectors into a population of host cells.

In a DNA or cDNA library, the pieces of DNA exist as an unordered collection of thousands or millions of pieces. To isolate a host cell carrying a specific DNA sequence (i.e., a specific DNA clone), the entire library must be screened. Radioactively labeled or otherwise labeled nucleic acid probes are traditionally employed to screen a DNA or cDNA library. Nucleic acid probes identify a specific DNA sequence by a process of in vitro hybridization between complementary DNA sequences in the probe and the DNA clone.

A specific DNA clone that has been identified and isolated in this manner can contain DNA that is contiguous to the probe sequence. A terminus of the DNA clone, therefore, can be used as a new probe to rescreen the same or another DNA library to obtain a second DNA clone which has an overlapping sequence with the first DNA clone. By obtaining a set of overlapping DNA clones, a physical map of a genomic region on a chromosome may be constructed. This process is called "chromosome walking" because each overlapping DNA clone which is isolated is one step further along the chromosome. Each DNA clone also can be studied to determine its genetic relationship to a previously mapped genetic function and, thus, a series of overlapping DNA clones provides a physical map of a chromosome which may be correlated to a map of genetic functions.

Chromosome walking is used, for example, to identify or localize a gene of interest, such as one thought to be causative of or associated with a disease or other condition, phenotype or quantitative trait. This is done by using a DNA fragment which displays a restriction fragment length polymorphism (RFLP) shown to be genetically linked to (i.e., physically localized to the same chromosome region as) a gene which causes or is associated with a disease, or other condition, phenotype, or quantitative trait or a segment of DNA contiguous to such a RFLP or a cDNA, as an in vitro hybridization probe to screen a DNA library and pull out larger fragments of DNA in which all or part of the probe sequence is represented.

The usefulness of any DNA clone isolated in this manner is that it includes DNA that is contiguous to the RFLP sequence that is incrementally closer to the position of the sought-after gene than the original RFLP. To get a step closer, a labeled molecule corresponding to an end of the newly isolated DNA clone is prepared and used to rescreen the library, with the goal being to isolate DNA clones that overlap with sequences found in the first DNA clone and that are incrementally closer to the gene of interest than either the starting probe or the first DNA clone isolated. This procedure is repeated as needed, with the resulting DNA clones being used in genetic studies to assess whether they are more closely linked to the gene of interest. To walk over a distance of 10 million base pairs using presently-available chromosome walking techniques could require from 100 to 2,000 steps, depending on the DNA cloning vector system used. Any approach designed to decrease the work required to take a single walking step or which would allow multiple walking projects to be carried out simultaneously would be a major advance.

The number of DNA clones which would be required to form a complete library of genomic DNA is determined by the size of the genome and the DNA clone capacity of the vector used to clone and propagate the segments of the genomic DNA. Construction and screening of genomic DNA libraries of organisms with large genomes is labor intensive and time consuming. The development of vectors having a capacity for large DNA clones has helped to reduce the labor involved in screening genomic libraries. However, screening libraries remains time consuming and labor intensive.

SUMMARY OF THE INVENTION

The present invention is a method of identifying and isolating a DNA fragment of interest (a target DNA fragment), from a DNA fragment library in a eukaryotic host cell, which is based on homologous recombination between the target DNA fragment and DNA present in a targeting DNA molecule introduced into the DNA fragment library. It further relates to targeting vectors and DNA fragment libraries constructed in eukaryotic host cells as described herein.

The method of the present invention is used to screen a DNA fragment library constructed in a eukaryotic host cell in which genetic recombination (exchange of information between DNA present in a chromosome in the host cell and DNA introduced into the host cell) occurs by means of homologous recombination. In one embodiment in which the eukaryotic host cell is yeast, genetic recombination occurs essentially exclusively by homologous recombination. DNA fragments in host cells are propagated in the form of artificial chromosomes which include, in addition to a DNA fragment insert, all of the DNA sequences necessary for the chromosome to participate in host cell replication and mitotic segregation in a manner similar to that of naturally-present host cell chromosomes. In general, the artificial chromosome is present in one copy or low-copy number in a host cell.

The present method makes use of a targeting vector or vehicle which: 1) includes a DNA sequence, referred to as targeting DNA, homologous to at least a portion of the target DNA fragment and a selectable marker gene which is functional in host cells under appropriate conditions and 2) is non-replicating in the host cell. Targeting DNA can be any DNA sequence, including genomic DNA, cDNA and DNA synthesized using known techniques. Preferably a double-strand break is made in the targeting DNA present in the targeting vector, which generally is circular when purified from an *E. coli* host. Alternatively, a gap can be introduced by making two cuts in the targeting DNA (e.g., with appropriately selected restriction enzyme(s)). The break or gap renders the vector linear, provides DNA ends which stimulate homologous recombination with host cell artificial chromosome sequences and increases the efficiency of stable transformation by homologous recombination.

The targeting vector is introduced into cells harboring the DNA fragment library, producing a mixed population of host cells, some of which contain the targeting vector and some of which do not. The resulting population of host cells is maintained under conditions appropriate for homologous recombination between DNA already present in the cell (i.e., prior to introduction of the targeting vector) and homologous sequences, such as those in the targeting vector. Subsequently, the population of cells is subjected to conditions appropriate for selection of host cells in which homologous recombination has occurred. Because the targeting vector is unable to replicate in the host cell, stable transformation with the selectable marker gene can occur only through homologous recombination. The selectable marker gene is replicated and, therefore, confers a stable phenotype, only in host cells in which homologous recombination with sequences that are replicatable in the host has occurred. Identification of such host cells—and, thus, of host cells containing the target DNA fragment of interest—is carried out by culturing the population of host cells under conditions (e.g., culturing on appropriate media) in which only those host cells in which homologous recombination (and stable transformation) occurred can survive. Growth of a transformed host cell is indicative of the presence of the target DNA fragment. Host cells containing a target DNA fragment are, as a result, separated or isolated from host cells which do not contain the target DNA fragment. The target DNA fragment can be removed from the host cell and sequenced or manipulated (e.g., subcloned or mapped), using known techniques.

Alternatively, targeting DNA and a selectable marker gene for selection in yeast can be introduced into yeast cells containing the DNA fragment library by mating a yeast strain containing the targeting DNA and the selectable marker gene on a targeting vehicle which is a replicating yeast linear plasmid with the yeast host cells containing the library. In this embodiment, the two yeast strains must be of opposite mating types. Homologous recombination occurs between the targeting linear plasmid and a library YAC having DNA homologous to targeting DNA, producing two linear molecules, each of which is a YAC. In one embodiment, the linear plasmid has negatively selectable markers flanking the targeting DNA sequence. Each of the two recombination products carries one of the two negatively selectable markers, making differential selection of the two recombination products possible. In another embodiment of the method in which mating of opposite mating type yeast strains is used, a first yeast strain containing a yeast replicating plasmid, constructed in such a manner that the targeting DNA and a first selectable marker gene can be freed from the yeast replicon by recombination events and a second selectable marker gene, which is a negatively selectable marker gene, is used to select the replicon itself. When this strain is mated to all members of a YAC library, the freed targeting sequence can undergo recombination with YAC molecules within the library.

The replicating yeast plasmids described above can also be introduced into host cells containing YACs by transformation.

In a preferred embodiment, the DNA fragment library is constructed in yeast, such as Saccharomyces (S.) cerevisiae or Schizosaccharomyces (S.) pombe, in which DNA fragments are present in yeast artificial chromosomes (YAC). Each yeast host cell contains one YAC or a few YACs, each present in one or few copies. A YAC includes, in addition to a DNA fragment, all of the DNA sequences required for chromosomes to replicate in yeast, segregate chromosomes to their progeny and stabilize chromosome ends. In this embodiment, the targeting vector used is a bacterial plasmid or other vector which does not replicate in yeast and includes targeting DNA and a selectable marker gene that functions in yeast. The targeting vector, which preferably has been linearized by introducing a double-strand break within the targeting DNA of the bacterial plasmid, is introduced into yeast cells. The resulting mixed population of yeast cells is maintained under conditions appropriate for homologous recombination to occur between targeting DNA and target DNA in the YAC. This is followed by selection of yeast cells stably transformed with the targeting DNA and selectable marker gene. Stable transformation of the yeast cells confers on them a selectable phenotype, such as antibiotic resistance, nutrient prototrophy (such as amino acid prototrophy or nucleoside prototrophy), tolerance to a metal ion, ability to progress through the cell cycle or expression of a cell surface marker. Growth of yeast cells under conditions compatible with survival only of stably transformed cells is indicative of the presence of the target DNA sequence. Target DNA can be removed from the yeast cell and sequenced or manipulated, using known techniques.

The present invention also relates to targeting DNA molecules and vectors useful in the present method. Vectors include targeting vectors, such as bacterial plasmids which do not replicate in yeast and include targeting DNA and a selectable marker gene functional in yeast. They may also include a selectable marker gene for selection in bacteria. Additional targeting DNA molecules include replicating molecules, such as a yeast linear plasmid.

YAC arm vectors useful in the present method are also the subject of the present invention. These include a yeast selectable marker gene, a bacterial origin of replication, a bacterial selectable marker gene, a yeast telomere, and one or more cloning sites at which targeting DNA is introduced or inserted into the vector. In addition, YAC arm vectors can include yeast centromere sequences and/or a yeast replication origin. YAC arm vectors which are the subject of the present invention include those designated pTKENDA, pTKENDA2, pTKENDB, pTKENDC, pTKENDD and their functional equivalents.

The present invention further relates to eukaryotic host cells, particularly yeast cells, constructed as described herein and useful for construction of YAC libraries from which a DNA fragment of interest can be identified and isolated by the claimed method. In addition, the present invention relates to DNA fragment libraries, particularly YAC libraries, constructed in such eukaryotic host cells.

The method, targeting vectors, YAC arm vectors and DNA fragment libraries of the present invention are useful for identifying and isolating a target DNA fragment, which can be genomic DNA or cDNA and can be an entire gene, gene portion or other DNA sequence. The DNA in DNA fragment libraries screened by this method can be of any type, such as, but not limited to, mammalian (particularly human), plant, insect, avian, fish, crustacean, molluscan, viral, nematode, amphibian, reptilian or protozoan. For example, they can be used to identify and isolate a gene associated with a particular disease, condition, phenotype, or quantitative trait, related genes within an organism's genome, and cDNA.

Further, as described herein, physically contiguous DNA sequences can be identified in a YAC library in yeast cells (or other DNA fragment library) and used to construct a physical chromosome map. That is, the present method is useful for chromosome walking. In this embodiment, a first YAC containing a target DNA fragment is isolated, using the claimed homologous recombination-based method described herein, and a terminus of the fragment is subcloned. In many instances, both termini will be subcloned in order to determine the correct direction for the walk to proceed. The terminus of the first target DNA fragment is then used as the targeting DNA present in the targeting vector, which is introduced into the YAC library. A second target YAC is isolated, which has as part of it the target DNA fragment, which partially overlaps the first target DNA in sequence. The second terminus is subcloned and used as the targeting DNA in a targeting vector introduced into the YAC library. This results in isolation of a third YAC containing a target DNA fragment, which partially overlaps the second target DNA fragment in sequence. This process results in isolation of a series of YAC containing target DNA fragments which partially overlap and can be repeated as many times as needed to construct the physical map sought. Chromosome walking can be carried out by the method of the present invention by using DNA which displays a restriction fragment length polymorphism (or RFLP), a DNA fragment contiguous to a RFLP or a cDNA, as targeting DNA in the targeting vector to screen a YAC library. A terminus of target DNA isolated in this manner is subcloned or isolated and the resulting sequence used to isolate a contiguous DNA fragment. This is repeated as often as needed to construct the physical map and, optimally, to reach a desired gene with which, for example, the RFLP is associated.

The method of the subject invention has numerous advantages over other approaches to screening DNA libraries. For example, it is possible to screen a DNA fragment library many times, simultaneously. Libraries are stored as a pool of clones, thus eliminating the work needed to organize and screen a library that is distributed over many filter membranes. The labor needed to screen a library is considerably less than that needed with conventional methods. In addition, terminal sequences are isolated from YAC clones without the need for subcloning in a form suitable for subsequent walking steps.

BRIEF DESCRIPTION OF THE DRAWINGS

FIG. 2 illustrates targeting (homologous reciprocal recombination) to generate a YAC that is marked for selection.

FIG. 3 illustrates selection by homologous recombination of a DNA clone from a DNA YAC library using one-step gene disruption.

FIG. 8a contains oligonucleotides used in the construction of YAC arm vectors SEQ ID NO:1–SEQ ID NO.:8. The sequences in upper case letters indicate bases corresponding to oligonucleotides synthesized in vitro. The sequences in lower case letters indicate those bases filled in in vitro using each pair of annealed oligonucleotides. Relevant restriction enzyme recognition sequences are indicated.

FIG. 8b contains oligonucleotides used in the construction of YAC arm vectors SEQ ID NO.:9–SEQ ID NO.:20. The sequences in upper case letters indicate bases corresponding to oligonucleotides synthesized in vitro. The sequences in lower case letters indicate those bases filled in in vitro using each pair of annealed oligonucleotides. Relevant restriction enzyme recognition sequences are indicated.

FIG. 8c contains oligonucleotides used in the construction of YAC arm vectors SEQ ID NO.:21–SEQ ID NO.:25. The underlined base indicates the mutation from the wild-type sequence.

BRIEF DESCRIPTION OF ATCC DEPOSITS

Figure 1:
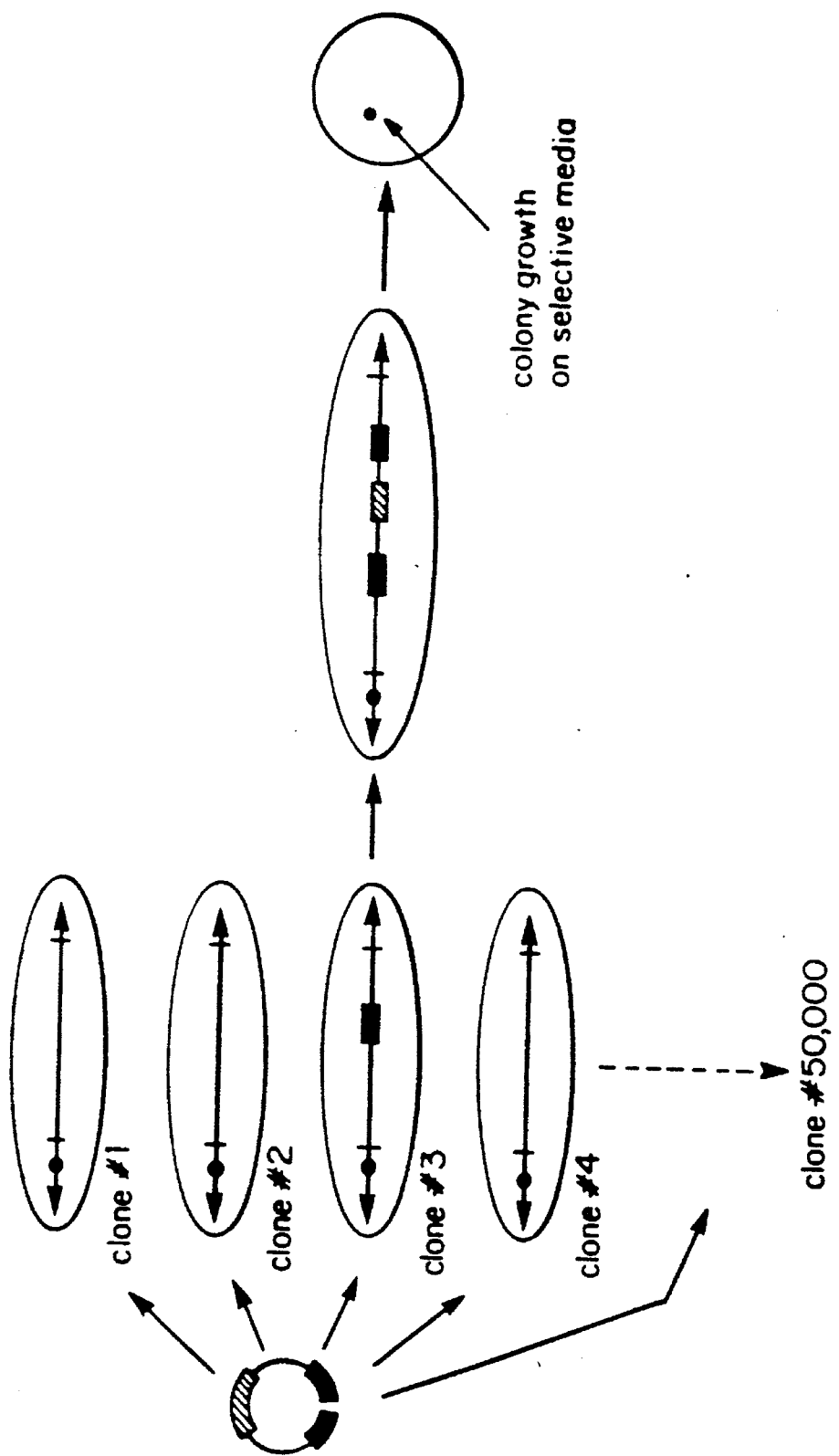
FIG. 1 illustrates the identification of target DNA fragments in a YAC library by the homologous-recombination selection method of the present invention. The YAC includes telomeres (arrowheads), centromere/yeast origin of replication (filled circles), and a DNA fragment; in the case of clone #3, the DNA fragment contains within it a target DNA fragment (solid rectangle).

The following deposits have been made at the American Type Culture Collections 12301 Parklawn Drive, Rockville, Md. 20852 (Jun. 28, 1990) under the accession numbers indicated. These deposits have been made under the terms of the Budapest Treaty and all restrictions upon their availability will be removed upon granting of a United States patent.

1. *Saccharomyces cerevisiae* strain TD7-16d, ATCC No. 74010.
2. Plasmid p184DLARG, ATCC No. 40832.
3. Plasmid pTKENDA, ATCC No. 40833.

DETAILED DESCRIPTION OF THE INVENTION

The present invention is based upon Applicant's discovery that the process of homologous recombination which occurs in eukaryotic cells can be used for the purpose of screening DNA fragment libraries constructed in eukaryotic cells and identifying and isolating a DNA fragment of interest, referred to as a target DNA fragment.

The present invention is a method of isolating a DNA fragment of interest, referred to as a target DNA fragment, from a DNA library constructed in a eukaryotic host in which genetic recombination occurs by homologous recombination. The target DNA fragment is generally present in a larger fragment contained in the eukaryotic host cell. The DNA used to construct the DNA libraries may be cDNA or genomic DNA which is of human or other origin, including that of plants and other mammals. A target DNA fragment is identified by the present method by introducing into the DNA fragment library a non-replicating targeting vehicle which contains targeting DNA and an appropriate selectable marker gene and identifying eukaryotic host cells in which homologous recombination occurs between target DNA and targeting DNA. Homologous recombination results in stable integration of targeting DNA and the selectable marker gene into DNA in host cells, which are identified on the basis of a selectable phenotype conferred as a result of stable transformation of host cells with the selectable marker gene. For example, they are identified on the basis of their ability to grow under conditions (e.g., in the presence of a drug or metal ion or in the absence of an essential nutrient) incompatible with growth of host cells in which stable integration has not occurred.

The DNA library used in the present method is a population of eukaryotic host cells, such as yeast cells, containing a unit, such as an artificial chromosome, which includes a DNA fragment insert and is replicated in the host cells. The DNA library is screened for DNA fragment insert(s), present in the artificial chromosome, all or a portion of which is a target DNA fragment, by introducing into the eukaryotic host cells a targeting vehicle, such as a bacterial plasmid, which is non-replicating in the eukaryotic host cells and includes a targeting DNA sequence (i.e., a DNA sequence homologous, at least in part, to the target DNA) and a selectable marker gene useful for selection in the host cell. Host cells containing the targeting vehicle are cultured under conditions appropriate for homologous recombination between the targeting DNA sequence and target DNA to occur. Host cells stably transformed with the selectable marker are subsequently identified (i.e., by identifying host cells able to grow under conditions under which non-stably transformed cells cannot grow, and die).

In general, the targeting vehicle is nonreplicating in the host cell, such as a bacterial plasmid, and includes the targeting DNA sequence and a selectable marker gene for selection in the host cell. However, in certain embodiments, such as those in which the host cell is yeast, the targeting vehicle may be replicating vehicle, such as a yeast linear plasmid, which includes marker genes for selection in yeast and targeting DNA.

In a specific embodiment of the present invention, which is exemplified by the Examples which follow, the DNA library is a population of yeast cells which contain artificial chromosomes carrying a DNA fragment insert and host cells containing target DNA are identified and isolated from this YAC vector library.

A targeting vehicle, such as a bacterial plasmid, which is non-replicating in yeast is introduced into the population of host yeast cells containing the DNA YAC library. The bacterial plasmid includes a targeting DNA sequence which is homologous, at least in part, to target DNA of interest and a selectable marker gene that functions in yeast. Preferably, the targeting plasmid is cut with a restriction endonuclease that introduces a double-strand break within the targeting DNA sequence, thereby linearizing the bacterial plasmid and providing DNA ends which are recombinogenic, to stimulate the process of homologous recombination with the YAC sequences. The efficiency of homologous recombination is, as a result, increased. Because the plasmid is non-replicating in yeast, stable transformation with the selectable marker can only proceed by integration into natural or artificial yeast chromosomes.

The resulting host yeast cell population, which includes stably transformed host yeast cells (i.e., those in which the plasmid, including the selectable marker gene, has been stably integrated by homologous recombination into DNA already present in host cells prior to introduction of the targeting vehicle) and non-stably transformed host yeast cells, is cultured under conditions such that only stably transformed yeast cells are able to grow. In a correctly targeted event, the entire plasmid is stably incorporated in the host yeast cells by homologous recombination between the targeting DNA sequence of the plasmid and homologous sequences (i.e., target DNA fragments) in the YAC. In other embodiments, such as that in which a linear targeting molecule is used, it is not necessary, however, for the entire plasmid to become stably incorporated, as long as homologous recombination occurs to an extent sufficient to introduce a selectable marker gene into DNA already present in the host cell, such as in a YAC. Only those few host yeast cells which contain a target DNA fragment(s) and have thereby undergone homologous recombination with the targeting plasmid are able to grow under the conditions used (e.g., in antibiotic-containing medium or medium lacking a nutrient essential to non-stably transformed cells), due to the introduction of the yeast-selectable marker gene contained on the targeting plasmid. They are identified on the basis of the selectable phenotype conferred by stable transformation of the selectable marker gene.

To prevent homologous recombination events between the plasmid-borne yeast-selectable marker gene and homologous sequences in the host yeast cells, it is preferable that host cell sequences homologous with targeting vector sequences have been deleted or almost entirely deleted from the genome of the host yeast strain before it is used for the YAC vector library. Alternatively, host cell sequences homologous with a yeast-selectable marker gene on the incoming targeting plasmid can be retained as a mutated, non-functional portion of the yeast chromosome. If this approach is used, however, more positive scores for homologous recombination will have to be screened to ensure that homologous recombination events which occur took place between the targeting DNA sequence on the bacterial plasmid and the target DNA sequence present on the YAC.

FIG. 1 illustrates schematically the isolation of target DNA fragments from a YAC vector library by the method of the present invention. The targeting plasmid on the far left is introduced into a population of yeast cells (ovals), each of which contains a DNA YAC containing a different DNA fragment. The plasmid includes a selectable marker gene for selection in yeast (diagonally lined section) and a targeting DNA fragment (solid section) in which a double strand break has been introduced. In this example, one host yeast cell (#3) contains a DNA fragment in a YAC that is homologous to a sequence carried on the targeting plasmid (solid sections on clone #3). Recombination between these two sequence occurs, resulting in the stable integration of the selectable marker carried on the plasmid into the yeast chromosome (YAC). The resulting population of cells is grown under conditions appropriate for selection of host yeast cells stably transformed with the selectable marker gene. For example, they are plated on appropriate selective media, such as nutrient deficient media. Only those cells in which the selectable marker gene functions grow. Growth of cells under these conditions is indicative of the presence of a target DNA fragment. Although YAC are exemplified herein, other yeast vectors, such as YCp vectors (YCp50, YCp19) can be used to construct a DNA library.

The general scheme for selection of a target DNA fragment from a DNA YAC library is shown in FIG. 2. FIG. 2 illustrates the integration of a targeting plasmid (p184DLARG) carrying a selectable marker (the yeast ARG4 gene; open box) and a segment of DNA that is homologous to a sequence in the DNA YAC library (targeting DNA; solid arcs on plasmid). The thin lines represent an insert of human or other (non-yeast) DNA propagated as a yeast artificial chromosome (YAC). The solid black box is the target DNA fragment, a sequence of DNA which is a portion of YAC DNA present in a DNA clone, found in the library, that is homologous to the targeting sequence. The remaining portions of the DNA YAC are comprised of the YAC vector arms: the thick lines represent plasmid vector sequences for replication and selection in bacteria. The shaded boxes represent genetic markers used for selection in yeast (yeast selectable markers URA3 and TRP1). The solid arrowheads and circle represent telomeres (TEL) and a centromere/yeast replication origin (CEN/ARS), respectively. FIG. 2a depicts the targeting DNA (present in the targeting vector) aligning with the target DNA fragment in the YAC. FIG. 2b depicts the product of homologous recombination between the targeting DNA and target DNA fragment. The targeting plasmid has been cut uniquely in the targeting DNA, at the site corresponding to the vertical arrow in the target sequence. ULL indicates the unit length linear restriction fragment that results from duplication of the target sequence (and the restriction site) on the YAC. As described in Example I, a ULL can be generated only if integration occurs into a DNA sequence that contains the restriction enzyme site in question and contains sufficient homology surrounding that site to allow resynthesis (by repair) of the restriction enzyme site on the targeting plasmid. Candidate clones that display a ULL are assumed to be homologous recombination events and are analyzed further.

In another embodiment of this method, a yeast-selectable marker gene on the incoming targeting DNA molecule can be a bacterial gene, engineered to be expressed in yeast, which confers drug resistance to yeast cells, e.g., the CAT or neo genes from Tn9 and Tn903, or bacterial amino acid or nucleoside prototrophy genes, e.g., the *E. coli* argH, trpC, and pyrF genes.

In another embodiment of the method of the present invention, the targeting vector is a linear DNA fragment which includes a targeting DNA sequence homologous to a target DNA fragment to be identified and/or isolated from the YAC library. In this embodiment, a selectable marker gene is inserted into the targeting DNA, producing a targeting DNA sequence which includes two non-contiguous domains. This embodiment is described in detail in Example II and represented schematically in FIG. 3. The targeting vector, which is a linear sequence which does not replicate in yeast, is transformed into the pooled DNA YAC library, as described in Example I. Homologous recombination occurs between the targeting DNA and the target DNA fragment.

In addition to the above-described embodiment, other approaches to introducing targeting DNA into host cells can be used. For example, targeting DNA can be present on a replicating yeast linear plasmid (Murray, A. W. and Szostak, J. W., *Nature* 305:189–193 (1983)) in a yeast strain of mating type opposite to that of the host strain used for the library. The linear plasmid has selectable markers flanking the targeting DNA sequence (i.e., one at each end of the targeting DNA); both markers are different from those used in the construction of the YAC library and can be selected against (i.e., negatively selectable markers, such as LYS2, URA3 or CYH2). Homologous recombination between two linear molecules produces two linear molecules, each of which is a hybrid of the two parental molecules. In this embodiment, in which recombination occurs between the targeting linear plasmid and a library YAC, each of the two recombination products is a YAC and each carries one of the two negatively selectable markers, allowing for differential selection of the two recombination products.

Figure 12:
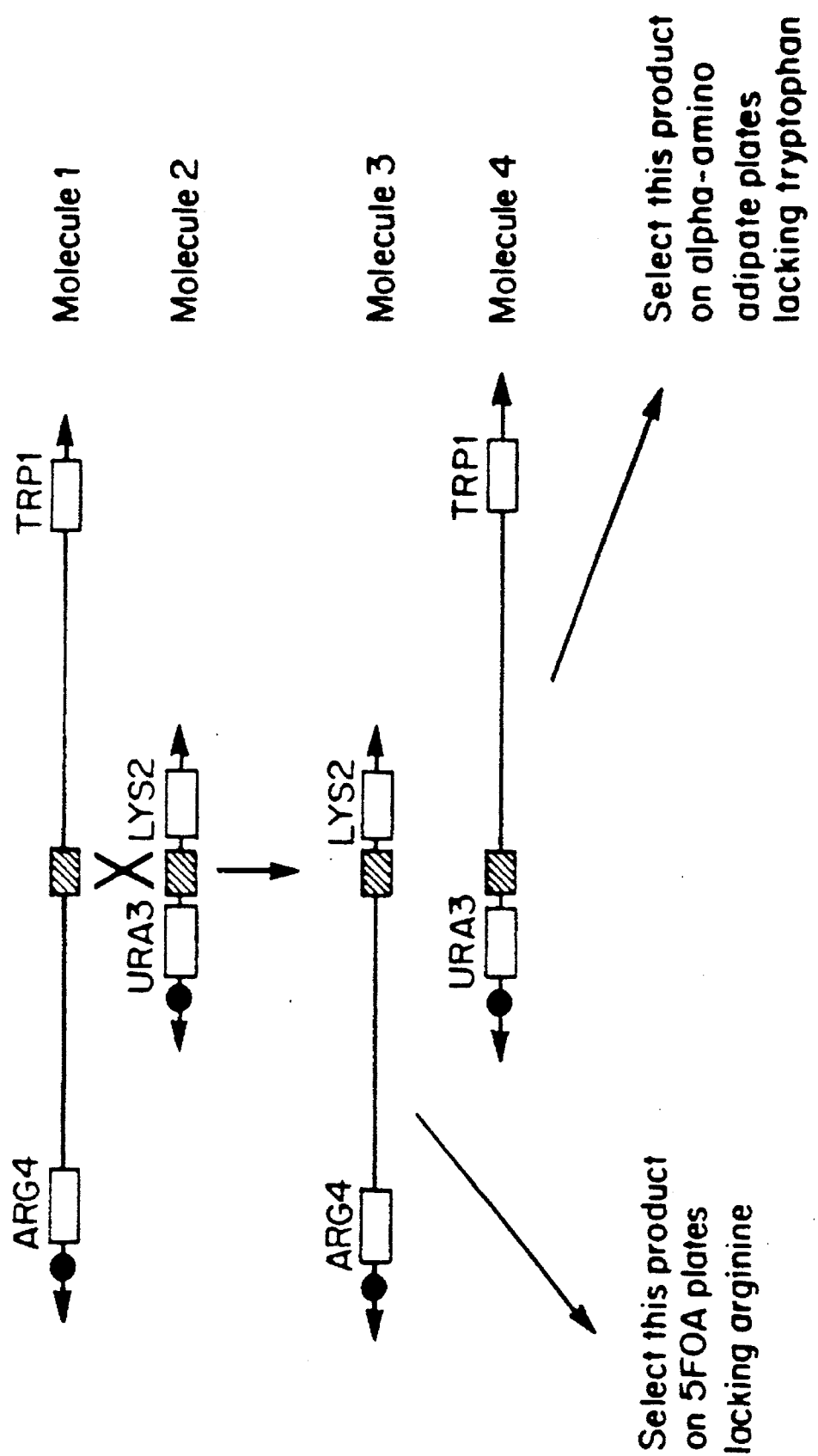
FIG. 12 is a schematic representation of one embodiment of the present homologous recombination method, in which a YAC containing target DNA is identified using recombination with a linear yeast plasmid.

The basis of this differential selection is illustrated in FIG. 12. Filled circles, arrowheads, and open rectangles represent centromeric, telomeric, and marker gene sequences, respectively. The shaded boxes represent targeting or target sequences. URA3$^+$ cells can be selected against (killed) by growth on media containing the nucleoside analog 5-fluoroorotic acid (5FOA), while LYS2$^+$ cells can be selected against by growth on media containing the amino acid analog alpha-amino-adipic acid ($\alpha$aa). Molecule 1 is a target YAC constructed in a vector system using ARC4 and TRP1 as selectable markers (phenotype arg$^+$ trp$^+$ 5FOA$^R$$\alpha$aa$^R$). Molecule 2 is a linear targeting plasmid in which the targeting sequence is flanked by URA3 and LYS2 (phenotype arg$^-$ trp$^-$ 5FOA$^S$ $\alpha$aa$^S$). The phenotype of cells harboring molecules 1 and 2 in an unrecombined form is arg$^+$ trp$^+$ 5FOA$^S$ $\alpha$aa$^S$. Molecules 3 and 4 are the products of recombination between Molecules 1 and 2, resulting from a cross-over between the targeting and target sequence. The phenotype of Molecule 3 is arg$^+$ trp$^-$ 5FOA$^R$ $\alpha$aa$^S$, and can be selected for by growth on 5FOA plates lacking arginine. The phenotype of Molecule 4 is arg$^-$ trp$^+$ 5FOA $\alpha$aa$^R$, and can be selected for by growth on $\alpha$aa plates lacking tryptophan. Thus, cells containing one or both non-recombinant molecules, as well as cells containing either of the recombinant products can be differentially selected (cells harboring only one or the other recombinant product arise by random loss events).

In such a scheme, the yeast cells harboring the targeting linear plasmids are mated to all members of the library and maintained under conditions favorable for spontaneous or induced homologous recombination (induced by, for example, meiosis or ultraviolet irradiation). Recombinant target YACs are selected by virtue of the unique phenotypes of the recombination products resulting from homologous recombination between the targeting sequence on the linear plasmid and YAC molecules harboring a suitable target sequence. Each of the two product YACs is truncated at the position of the target DNA sequence, and the differential selection is used to isolate the two products separately. In order to isolate the two products of the single event, yeast cells harborings YACs and linear targeting plasmids are preferably plated or gridded out prior to selection for recombinants. Selection is accomplished by replica plating onto the appropriate selective plates.

In this embodiment, the relative orientation of the targeting sequence with respect to the two (negatively) selectable markers on the linear targeting plasmid is important. Recombination between a target YAC and only one of the two orientations of targeting linear plasmid will give rise to a stable recombinant (i.e., a recombinant with one and only one centromere). YAC molecules with two centromeres show frequent breakage and unstable phenotypes; YAC molecules with no centromere are highly unstable by virtue of segregation bias. In one embodiment, linear targeting plasmids are constructed with the targeting sequence present in both orientations and introduced into the library in separate matings.

As an alternative to mating to introduce linear targeting plasmids into the library, linear targeting plasmids can be introduced into host cells containing YACs by transformation, essentially as described in Example I.

In another embodiment, a yeast replicating plasmid carrying a targeting sequence can be constructed in such a manner that the targeting DNA and a selectable marker (SM1) can be freed from the yeast replicon by natural or induced recombination events, and such that the replicon itself can be selected against by virtue of a negatively selectable marker (SM2), such as URA3, LYS2 or CYH2. Examples of inducible recombination systems which can be engineered to function for this purpose are the flp mediated recombination pathway of the yeast 2-micron plasmid and the cre-lox recombination system of bacteriophage P1. The plasmid is introduced into a yeast strain of mating type opposite to that of the host strain used for the library. After mating to all members of the YAC library, the targeting DNA sequence and selectable marker are released as a non-replicating molecule and the selectable marker can only be stabilized by homologous recombination with a YAC harboring a suitable target DNA sequence. The targeted recombinants are selected by plating onto media which selects for SM1 and against SM2.

As an alternative to mating to introduce the plasmid described in the preceding paragraph, the plasmid can be introduced by transformation, eseentially as described in Example I, followed by the induction step to free the targeting substrate from the yeast replicon.

Identification and Isolation of a Target DNA Fragment Using Homologous Recombination The above-described embodiments of the present method are useful to identify and isolate any target DNA fragment, which can be an entire gene, a gene portion or other nucleotide sequence. For example, a gene of interest, such as a β-globin gene or adenosine deaminase gene, can be identified in a DNA fragment library using the claimed method and, if desired, isolated from host cells by known methods. Identification of target DNA fragments by the present method is described in detail in Examples I, V and VI.

Homologous-Recombination Chromosome Walking

The method of the present invention, by which a target DNA fragment is isolated from a DNA library, is useful for isolating physically-contiguous DNA segments from a DNA YAC library in order to construct a physical chromosome map. That is, when used iteratively, each time with targeting DNA derived from a YAC which overlaps with and extends beyond a previously identified region, it is a method for chromosome walking. In the present method of chromosome walking, a target DNA fragment present in a YAC is isolated, as described above. A terminus of this first target YAC fragment is subcloned into a plasmid vector. The terminus of the first DNA fragment is, thus, used as a second targeting DNA sequence, which is introduced into host yeast cells containing a DNA YAC library. The terminus of the first DNA fragment, which is contiguous to the first target DNA sequence, in turn becomes the second targeting DNA sequence. As used herein, the term contiguous includes sequences which are immediately adjacent to the first target sequence and those nearby or in proximity to the first target sequence (i.e., separated from the first target sequence by intervening nucleotide(s)). This second targeting DNA sequence should not have any homology with the first targeting DNA sequence, so that when it in turn is incorporated in a YAC at a point of homology with a second DNA clone, the second DNA clone selected will have a different terminal DNA sequence. The terminal subfragment from the second DNA clone is used to isolate the next (i.e., the third) DNA clone. Each successive DNA clone is isolated by virtue of its homology with the terminal subfragment of the previously isolated DNA clone. A series of overlapping clones is obtained by repeating this process; the process is repeated as needed to construct the physical map desired. The successive recovery of terminal DNA fragments allows rescreening the same library or a second library for overlapping clones.

In one embodiment of the present invention, chromosome walking is carried out in order to determine the chromosomal location of a gene of interest, such as a gene which causes a disease, by using a DNA fragment displaying a RFLP genetically linked to the gene of interest, or a fragment contiguous with the RFLP, as targeting DNA in the targeting vector. A targeting vector, such as a bacterial plasmid, which includes the RFLP-displaying DNA, or fragment contiguous to the RFLP displaying DNA, or cDNA as targeting DNA and a selectable marker gene, is introduced into a human DNA YAC library. Homologous recombination between the targeting DNA and a target DNA fragment in the library results in the first step in walking to the gene of interest. A YAC containing the target DNA fragment is identified in this way. One terminus or both termini of the target DNA fragment is used as targeting DNA in a targeting vector to rescreen the same library or screen a second library, as described above. Also as described above, this is repeated, each time using a terminus of the target DNA fragment isolated in the previous step as targeting DNA. This continues until the gene of interest is identified or the desired physical map is completed.

In another embodiment of the present method of homologous-recombination chromosome walking, the terminal fragments from the DNA YAC inserts can be isolated by a plasmid-rescue technique. This embodiment is described in detail in Example III and represented schematically in FIG. 4. In this case, the YAC vectors are designed such that the YAC vector arm contiguous to the DNA fragment (clone)

insert terminus contains sequences which allow for plasmid replication and selection in a bacterial host. Restriction enzyme digestion of the selected YAC DNA clone produces a fragment with one end lying within the terminus of the DNA clone sequence and extending into the YAC vector arm. This fragment contains the bacterial plasmid sequences which are essential for replication and selection in *E. coli*, covalently linked to a fragment of DNA from the terminus of the selected YAC DNA clone. Plasmid rescue involves restriction enzyme digestion of the total yeast DNA from the selected yeast clone; ligation of the digested yeast DNA to form monomer circles; and transformation of this ligated DNA mixture into *E. coli*, with the selection for the marker gene in *E. coli*.

Figure 4A:
FIG. 4 illustrates selection of DNA clones by homologous recombination using two DNA YAC libraries.
Figure 4B:
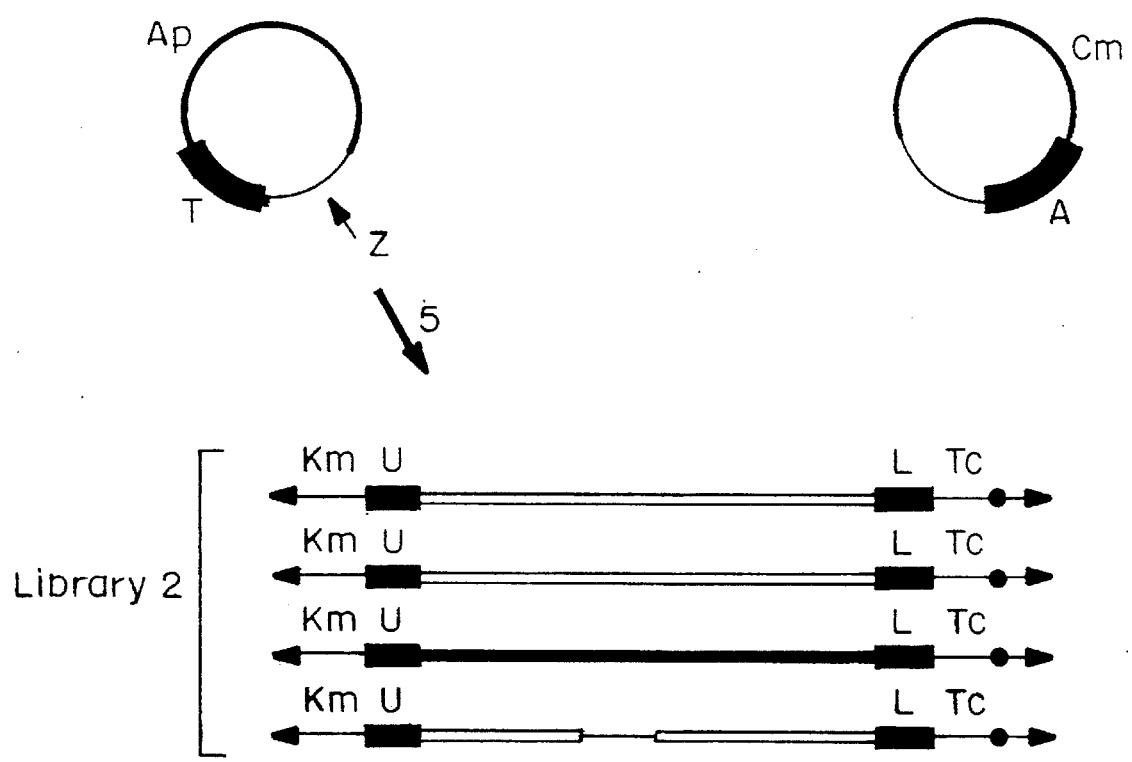

For use in conjunction with the plasmid rescue technique, one can design two different DNA YAC libraries. Each library will utilize a different pair of selectable markers. A set of four YAC arms are designed containing appropriate selectable markers for the two different libraries. Each YAC arm contains a yeast-selectable marker that would be appropriate for the selection of host yeast cells of the other library. In FIG. 4, the yeast-selectable markers in Library 1 are ARG4 and TRP1 and in Library 2 they are LEU2 and URA3.

Total yeast DNA from cells containing the first targeted DNA YAC clone are digested with a restriction endonuclease that separates the sequence conferring replication and stability function in yeast from the region of the YAC cloning vector that allows selection and propagation in bacteria and a selectable marker that functions in yeast (step 3 in FIG. 4). This region remains covalently attached to sequences containing the first targeted DNA fragment terminus. This fragment of the YAC DNA clone terminus contains sequences necessary for replication in bacteria, a selectable marker for selection in bacteria, and a selectable marker for selection in yeast, along with the first targeted DNA clone terminus sequence. This fragment is circularized and amplified in bacteria (step 4 in FIG. 4). This product then becomes the targeting plasmid with which to transform the second DNA library, after introducing a double-strand break within the sequence corresponding to the DNA clone terminus (i.e., within the trageting DNA sequence) (steps 5 and 6 in FIG. 4). The two DNA YAC libraries, Library 1 and Library 2, are constructed so that the arms in each are stabilized by a different vector sequence, with each arm having a unique selectable marker for selection in yeast and a unique selectable marker for selection in bacteria.

The rescue of DNA clone termini described in Example III utilizes restriction endonucleases to cleave a DNA clone in such a manner that the terminus is covalently attached to a fragment of the YAC vector arm. One of ordinary skill in the art will know how to isolate DNA clone termini by use of various embodiments of the polymerase chain reaction (PCR) (for example, inverse PCR or anchored PCR) with such reaction using at least one unique primer that anneals to the YAC vector arm immediately adjacent to the DNA cloning site, such that the first strand synthesis proceeds away from the YAC vector arm and copies cloned. DNA, and in which specific restriction enzyme cleavage sites comprise part of one or both of the PCR primers which would facilitate the subcloning of terminal fragments from DNA YACs.

Even in the absence of homologous recombination screening, a two library system is particularly useful for chromosome walking. Two key characteristics of such a two library system are that: 1) among the total of four arms which must be present in the final two libraries, no arm shares the same marker for plasmid selection in *E. coli* and 2) there is limited or no homology between the bacterial plasmid replicons used in the two different libraries.

In this system, the two unique terminal sequences from clones isolated by plasmid rescue (see Example III) from the first YAC library (Library 1) can be isolated independently simply by plating on different selective media plates. Since the isolated plasmids harboring the terminal sequences have limited or no homology to either vector arm present in the second YAC library (Library 2), these plasmids can be used in traditional filter hybridization screening without subcloning the terminal sequences from the plasmid. The plasmids rescued in *E. coli* can be purified and labeled (e.g., by nick-translation or random hexamer priming), and used directly to screen a second library. YAC clones isolated from Library 2, themselves isolated by screening with intact rescued plasmids carrying terminal sequences from YAC clones isolated from Library 1, represent steps taken in a chromosome walk. Each walking step thus proceeds by using labeled plasmids derived from the ends of YAC molecules isolated from one of the two libraries to directly screen the other, complementary, library. This method greatly improves the efficiency of traditional filter screening techniques by providing a rapid method for independent isolation of each of the two YAC termini by differential selection in forms suitable for direct labeling and library screening. It eliminates the need to subclone or otherwise purify terminal fragments for the purpose of labeling and screening for overlapping YAC clones.

The design of the YAC vector arms and the restriction enzymes used for plasmid rescue should be such that the yeast selectable marker (as well as the centromeric, telomeric, and yeast replication sequences) is separated from the rescued plasmid sequences and the YAC clone terminus. This eliminates the need to use different yeast selectable markers in the construction of Libraries 1 and 2, and to construct a host yeast strain with complete deletions of the selectable markers used to select for YAC clones in Libraries 1 and 2. Unique selectable markers for each of the four arms, which make plasmid selection in *E. coli* possible, can be, for example, a gene encoding resistance to an antibiotic, such as chloramphenicol, kanamycin, ampicillin, tetracycline, spectinomycin, streptomycin, or erythromycin, or a gene encoding a biosynthetic marker for which a suitable auxotrophic host exists.

Bacterial replicons which can be used in order to limit the homology between those in the two libraries are, for example, p15A, ColE1, phage M13, phage fl, phage Lambda and their equivalents.

Host Cell Types and Characteristics

The method is described herein with particular reference to screening YAC DNA libraries constructed in yeast cells through the use of targeting DNA sequences present in bacterial plasmids. It is to be understood, however, that this is merely for purposes of exemplification and that the present method can be carried out using other host cell types, provided that genetic recombination between vector-borne DNA and DNA already present in the host cell occurs by homologous recombination and that an appropriate non-replicating targeting vector is available.

Appropriate eukaryotic host cells include those which normally (as they occur in nature) undergo genetic recombination essentially exclusively by homologous recombination (e.g., *Saccharomyces cerevisiae*, *Schizosaccharomyces pombe*). As used herein, the term essentially exclusively means that homologous recombination occurs without significant levels of non-homologous recombination under the conditions used.

Homologous-recombination selection of DNA clones could be utilized as a selection method in the cells of any organism in which 1) a suitable DNA cloning system exists and 2) the cells can be manipulated or induced by genetic engineering or genetic manipulation to perform recombination which is predominantly based on DNA sequence homology, or in which the targeting DNA can be treated in such a manner that it engages in homologous-recombination as its preferred mode of recombination. With these criteria met, one skilled in the recombinant DNA arts could perform homologous-recombination selection of DNA clones from a DNA library. Such organisms may include, but are not limited to, *Schizosaccharomyces pombe, Drosophila melanogaster, Homo sapiens, Mus musculus* and *Spodoptera frugiperdea*.

*Saccharomyces cerevisiae* is a preferred host organism for the selection of DNA clones using homologous-recombination because of its ability to route transforming DNA carrying double-strand breaks into a recombination pathway based virtually exclusively on DNA sequence homology.

Certain characteristics of host cells in which DNA fragment libraries are constructed should be considered and possibly modified to optimize use of such cells in the present method, such as by decreasing non-targeted events and, thus, increasing the efficiency of the method. For example, as described below, it might be necessary to remove selectable markers present in the targeting vector from host yeast cells and to construct targeting vectors in such a manner that they include no sequences homologous with those in the vector sequences used in the propagation of the DNA library.

As described below, it has been determined that the selectable marker gene(s) chosen for the targeting vector should not normally be present in the host yeast genome or should be deleted from normal chromosomal position(s) in the host yeast strain. Without this modification of the host strain, recombination events between the selectable marker and the yeast genome would occur at a higher rate. For near-complete (>99%) coverage of the human genome, a DNA YAC library with an average fragment size of 300 kb would consist of approximately 50,000 members (Maniatis, T. et al., *Molecular Cloning-A Laboratory Manual*, pg 271, Cold Spring Harbor Laboratory Press, Cold Spring Harbor, N.Y., 1982). In order to isolate sequences that are represented only once in such a library, the ratio of targeted to non-targeted events should approximate or exceed 50,000 to 1, for at this ratio one incorrect (non-targeted) clone will be isolated for every correct clone. In most cases, however, sequences in this library will be represented 3–5 times, and a ratio of 10,000–17,000 to 1 would be adequate. Non-targeted events result from recombination between the targeting plasmid and regions of homology in the yeast genome, and can be minimized by decreasing the extent of such homology. As described in Example VII, it was determined that deleting the chromosomal copies of selectable marker genes present on the vectors used is desirable because it reduces the occurrence of non-targeted events. As described in Example VII, these results indicate that the selection of a targeted clone (target DNA fragment) from a DNA YAC library is feasible and particularly efficient in host yeast cells that carry no homology with selectable markers present on targeting vectors.

Non-targeted events might also occur as a result of homologous recombination between sequences on the targeting vector, such as the bacterial plasmid origin of replication or drug resistance marker, and homologous sequences on the YAC vector arms used to construct the DNA library. This homology can be minimized by constructing the targeting vector using a drug resistance marker that is not present in the YAC vector, and by using a bacterial plasmid origin of replication that is divergent from or non-homologous to the origin present on the YAC vector arms. The results described in Example VII also place the frequency of non-homologous recombination at approximately 0.003% (1 in 30,729), consistent with the invention described in this application. It was possible to select yeast cells carrying homology to the targeting vector even when only 1 in 10,000 of the cells transformed had such homology. In fact, at this dilution targeted events were isolated multiple (four) times, indicating that a clone represented once in a library of 40,000 clones could be isolated.

Targeting Vectors

Targeting vectors or vehicles useful in the method described herein are also the subject of the present invention. One type of targeting vector of the present invention has two key characteristics: the vectors are non-replicating in the host cell in which the DNA fragment library is constructed and include a DNA sequence, referred to as targeting DNA, which is homologous at least in part to a target DNA fragment which, for the purposes of the invention, is a DNA fragment comprising all or a portion of a desired clone to be identified in and isolated from the DNA library. Targeting vectors will generally be bacterial plasmids of the YIp class, particularly in those cases in which yeast cell hosts are used. Vectors appropriate for other types of cell hosts can also be constructed using known techniques.

Sequences used as targeting DNA in the targeting vector can be entirely homologous to the target DNA fragment, although they need not be. They need be only sufficiently homologous that under the conditions used, genetic recombination between vector-borne DNA introduced into the cells and DNA in YAC in the cells occurs by the host cell recombination pathway or process. Preferably, a double strand break or gap is introduced into a targeting DNA sequence. The free ends adjacent to the break or gap can be modified to prevent recircularization (e.g., by phosphatase treatment of the ends of the DNA, by creating non-complementary ends by using two different restriction enzymes or by removing nucleotides from one strand of the DNA, producing a single stranded tail). A survey of the literature reveals that single-stranded (3') overhangs are intermediates in genetic recombination in yeast and other species (Sun, H. et al. *Cell*, 64:1155–1161 (1991); Maryon, E. and Carroll, D. *Mol. Cell. Biol.* 11:3268–3277). It is reasonable to expect that the use of DNA modifying enzymes that degrade one strand of a DNA duplex (such as the strand with 5'→3' polarity) on one or both sides of a double-strand break in this case, resulting in molecules with single stranded 3' overhangs on one or both sides of a double-strand break or gap) may be useful in producing substrates that have enhanced ability to function as targeting molecules in homologous recombination library screening.

In addition to targeting DNA, targeting vectors include a selectable marker gene that functions in yeast, an origin of replication and a selectable marker that functions in bacteria (e.g., *E. coli*.). The selectable marker gene is one which is functional (makes selection of transformed cells possible) in the host cell type used for DNA fragment library construction. The choice of the yeast selectable marker gene can be made from among many various endogenous yeast gene loci, e.g., ARG4, LEU2, HIS3, HIS4, THR1, URA3, TRP1, LYS2, ADE2, ADE8, and MET2. Alternatively, the yeast selectable marker may be a marker gene that is not endogenous to the yeast genome, but is a foreign gene that confers a selectable phenotype, e.g., a bacterial gene engineered to be expressed in yeast and confer drug resistance on the yeast cells (such as the CAT or neo genes from transposons Tn9 and Tn903, respectively) or nutrient prototrophy, such as amino acid or nucleoside prototrophy (such as *E. coli* argH, trpC, or pyrF genes). Other selectable marker genes useful for this purpose include genes which confer tolerance to metal ions (e.g., the CUP1 gene, which confers resistance to copper ions), genes which confer an ability to progress through the cell cycle on cells with a mutant phenotype and genes which result in expression of a cell surface marker.

The suitable selectable marker genes for selection in bacteria include the genes encoding resistance to the antibiotics, chloramphenicol, kanamycin, ampicillin, tetracycline, spectinomycin, streptomycin, erythromycin, or any other marker, including genes encoding biosynthetic enzymes for which auxotrophic bacterial hosts exist.

Bacterial origins of replication may be derived from a variety of sources, including p15A (exemplified by the origin of plasmid pACYC184), ColE1, phage M13, phage f1, phage Lambda, or any other replicon that one trained in the art would recognize as providing an equivalent function.

Vectors constructed and used to screen YAC DNA libraries are described in detail in Example III and represented schematically in FIGS. 5 and 6a–6d. Targeting plasmid p184DLARG contains a selectable marker functional in yeast (ARG4) and a bacterial origin of replication (derived from pACYC184).

Targeting DNA molecules are not limited to molecules of the YIp class. The targeting DNA can be a fragment of DNA purified from a larger plasmid, with such a plasmid constructed in such a manner that the desired targeting sequence is interrupted by, among other sequences, a bacterial or yeast replicon. The plasmid is also constructed in such a manner that upon cleavage with a restriction enzyme that will release the replicon from the inner section of the targeting sequence, a yeast selectable marker remains covalently linked to the outer two ends of the targeting sequence.

Alternatively, a selectable marker and a targeting sequence can be ligated together in vitro, and ligation products consisting of one copy of the targeting sequence and one copy of the selectable marker (or multimers consisting of alternating targeting and selectable marker sequences in a uniform orientation) are purified. These ligation products are circularized in vitro and cleaved with a restriction enzyme to introduce a double-strand break of gap in the targeting sequence and leaving the selectable marker intact.

Finally, the two halves of a targeting sequence can be ligated to a selectable marker in a single three-way ligation in vitro to generate a targeting molecule suitable for transformation.

Yeast Arm Vectors

Yeast arm vectors or YAC arm vectors, which are used to produce yeast artificial chromosomes, are also the subject of the present invention. YAC arm vectors include a yeast selectable marker gene, a bacterial origin of replication, a bacterial selectable marker gene and a yeast telomere. They may additionally include a yeast replication origin (ARS) and/or a yeast centromere sequences. The components of these YAC arm vectors can be obtained from sources in which they occur naturally or can be produced using recombinant or genetic engineering techniques or chemical synthesis. For example, the telomere sequences, centromere sequences and ARS can be obtained from yeast or from another organism. It is only necessary that they function in yeast host cells as, respectively, a telomere, a centromere or an ARS. Components which have equivalent functions, regardless of their source (e.g., yeast or other source) are referred to herein as functional equivalents of the corresponding yeast element.

The present invention is illustrated by the following Examples, which are not intended to be limiting in any way.

Methods Used Herein

Unless otherwise noted, methods for plasmid purification, restriction enzyme digestion of plasmid DNA and gel electrophoresis, use of DNA modifying enzymes, ligation, transformation of bacteria, transformation of yeast by the lithium acetate method, preparation and Southern blot analysis of yeast DNA, tetrad analysis of yeast, preparation of liquid and solid media for growth of *E. coli* and yeast, and all standard molecular biological and microbiological techniques can be carried out essentially as described in Ausubel et al. (Ausubel, F. M. et al., *Current Protocols in Molecular Biology*, Greene Publishing Associates and Wiley-Interscience, New York, 1987).

EXAMPLE I

SELECTION BY HOMOLOGOUS-RECOMBINATION OF A TARGETED DNA CLONE FROM A DNA YAC LIBRARY

Plasmid pYAC4 (ATCC #67380) was used to construct a library of human genomic DNA. Human DNA was isolated from white blood cells (D. Burke, Ph.D. Thesis, Washington University, St. Louis, Mo., 1988), partially digested with EcoRI and ligated to pYAC4 arms digested with EcoRI and BamHI.

The ligation mixture was then used to transform yeast host strains, either MGD131-10c or IV-16d, using the spheroplast method (Burgers, P. M. J. and Percival, K. J. (1987) *Analytical Biochemistry* 163:391–397). (The construction of host strains MGD131-10c and IV-16d with the appropriate marker deletions is described in Example III below.) Since the pYAC4 vector carries the yeast selectable markers TRP1 and URA3, transformants can be selected for by growth on plates lacking tryptophan and uracil. 11,625 YACs with an average size of 190 kb (0.73 human genome equivalents) are individually grown in the wells of 96-well microtiter plates; 0.1 ml was taken from each well and pooled in three subpools of approximately 4,000 clones each. For each subpool, an equal volume of 30% glycerol was added and the subpool was aliquoted and frozen at −70° C.

For a library comprising 73% of one genome, and assuming equal representation of all clones, the probability that it contains any one specific human DNA sequence is just over 0.5. The probability that one of six different fragments of DNA is represented in the library is $1-(0.5)^6$, or 0.98.

Figure 5:
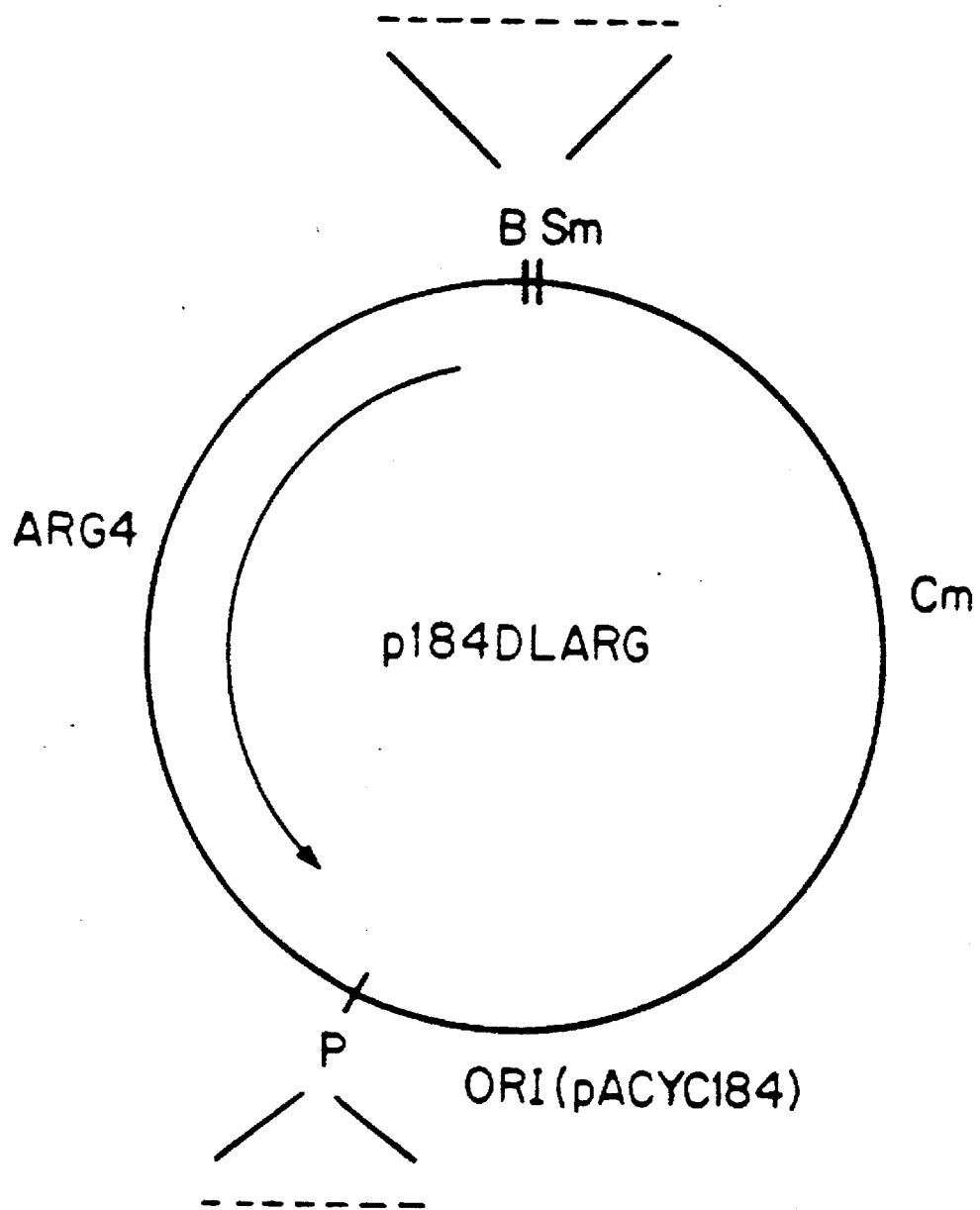
FIG. 5 is a map of plasmid p184DLARG. B: BamHI; Sm: SmaI; P: PstI; ARG4: yeast ARG4 gene (arrow indicates direction of transcription); Cm: chloramphenicol resistance gene; ORI (pACYC184): Origin of replication from pACYC184; - - - : hypothetical targeting sequence inserted into cloning site.

The construction of the targeting plasmid p184DLARG is described below and illustrated in FIG. 5. It carries the yeast ARG4 gene (Beacham, I. R. et al. (1984) *Gene* 29:271–279) as a selectable marker, and its bacterial origin of replication is derived from pACYC184 (Chang, A. C. Y. and Cohen, S. N. (1978) *Journal of Bacteriology* 134:1141–1156.), which shares only limited sequence homology to the pBR322 origin used on pYAC4. The entire chromosomal copy (a 2.0 kb HpaI DNA fragment) of ARG4 has been deleted in the library host strains IV-16d and MGD131-10c. The 2.2 kb BclI-ClaI fragment from pACYC184 (Chang, A. C. Y. and Cohen, S. N., (1978), *Journal of Bacteriology* 134:1141–1156.) containing the p15A origin of replication and the chloramphenicol resistance gene was ligated to BamHI-AccI digested pMLC28 (a derivative of pSDC12 carrying the pUC18 multiple cloning site; Levinson et al., *J. Mol. Appl. Gen.*, 2:507–517 (1984); plasmid pUC18 (ATCC #37253) can substitute for pMLC28 in the construction of p184DLARG described here). BamHI and AccI cut this plasmid one time each, in the polylinker. The ligation mixture was digested with SacI and HindIII, which cut in the PMLC28 polylinker, and the digested DNA was treated with T4 DNA polymerase to generate blunt ends. The DNA was ligated under dilute conditions to promote circularization, and the ligation mix was treated with the restriction enzyme AvaII (to linearize any parental molecules) prior to transformation into bacteria. One plasmid, p184DL, carrying only the sequences contained within the larger of the two BclI-ClaI fragments of pACYC184 and a permuted version of a portion of the pMLC28 polylinker was identified. Plasmid pHpa5 (provided by N. Schultes and J. Szostak; Department of Molecular Biology, Massachusetts General Hospital, Boston, Mass. 02114) carries the ARG4 gene as a 2.0 Kb HpaI fragment inserted into the HincII site of pMCL12 (a derivative of pSDC12 carrying the pUC12 multiple cloning site). Levinson et al., *J. Mol. Appl. Gen.*, 2:507–517 (1984). This plasmid was cut at the PstI and SmaI sites flanking the ARG4 insert, and the ARG4 fragment was ligated to PstI-SmaI cut p184DL. A plasmid carrying a single copy of the ARG4 gene inserted in the orientation shown in FIG. 5 was isolated and designated p184DLARG. FIG. 5 is a map of plasmid p184DLARG.

Genomic fragments for tyrosine hydroxylase (chromosome 11), metallothionein II pseudogene (chromosome 4), anonymous DNA markers D16S3 and D16S37 (chromosome 16), and a 1.9 kb HindIII fragment located 5' of the epsilon globin gene (chromosome 11) were subcloned into p184DLARG and used for selection of clones by recombination from a YAC library. With the exception of the tyrosine hydroxylase gene fragment, all of the fragments were blunt ended by treatment with T4 DNA polymerase and ligated to SmaI cut p184DLARG. The tyrosine hydroxylase gene fragment was cloned into the BamHI site of p184DLARG. A 103 kb HpaI-BamHI fragment from the 5' end of the beta globin gene (chromosome 11) was blunt-end ligated to the same 2.2 kb BclI-ClaI fragment used to construct p184DLARG. The beta- and epsilon-globin fragments are 1.3 and 1.9 kb fragments, respectively, from the human beta-hemoglobin locus on chromosome 11. The beta-globin fragment (ATCC #39698) was subcloned from pHU5'beta (Treco, D., et al., *Mol. Cell. Biol.*, 5:2029–2038, 1985), and includes sequences from positions 61,338 (HpaI site) through 62,631 (BamHI site) in the Genbank HUM-HBB sequence. This fragment includes the 5' end of the human beta-globin gene. The AvaII site at Genbank map position 62,447 was used to introduce a double-strand break for targeting, leaving 1.1 and 0.18 kb of homology on either side of the break. The 5' epsilon-globin probe (ATCC #59157), is a HindIII fragment and includes sequences centered approximately 15 kb 5' to the epsilon-globin gene (ATCC 59157), from positions 3,266 through 5,172 in the Genbank HUMHBB sequence. The ApaI sites at map positions 4,361 and 4,624 were used to create a 0.26 kb double-strand gap for targeting, leaving 1.1 and 0.5 kb of homology on either side of the gap.

Properties of the remaining four genomic DNA fragments are as follows: tyrosine hydroxlase (chromosome 11; 2.3 kb BamHI fragment: ATCC #59475; double-strand break made with HindIII, 0.6 kb from end); metallothionein pseudogene (chromosome 4; 2.8 kb HindIII-EcoRI fragment; ATCC #57117; double-strand break made with NdeI, 0.4 kb from end); anonymous DNA marker D16S3 (chromosome 16; 1.5 kb HindIII fragment; ATCC #59447; double-strand break made with ApaI, 0.75 kb from end); D16S37 (chromosome 16; 2.3 kb HindIII fragment; ATCC #59189; double-strand break made with ApaI, 0.95 kb from end).

Each targeting plasmid was linearized with a restriction enzyme that cuts within the human DNA (the targeting DNA) and 20 μg of digested DNA was used to transform the pooled library. Equal volumes of the three library subpools were thawed, mixed and inoculated into CM-ura-trp medium containing 40 μg/ml each of kanamycin and ampicillin. This culture was grown overnight at 30° C. with vigorous shaking and harvested at a density of $1.86 \times 10^7$ cells/ml. The cells were transformed using the lithium acetate method (Ausubel, F. M. et al., *Current Protocols in Molecular Biology*, Supplement 5, Greene Publishing Associates and Wiley-Interscience, New York, 1987). 20 μg of plasmid cut within the human DNA was used to transform $7 \times 10^8$ cells in a volume of 0.2 ml, and the entire transformation mix was spread onto the surface of eight selective plates (complete minimal media lacking uracil, tryptophan, and arginine) and incubated at 30° C. for 3–7 days.

Transformants were analyzed by restriction enzyme digestion and Southern hybridization analysis. DNA was prepared from each of the candidates and digested with the same enzyme used to linearize the targeting plasmid. The Southern blot was probed with $^{32}P$ radiolabeled ARG4 DNA. Homologous integration events are identified by hybridization to a single band of exactly the same size as the linearized transforming DNA molecule [the "Unit Length Linear" band (ULL); FIG. 2]. A ULL can only be generated if integration occurs into a DNA sequence that contains the restriction enzyme site in question, and contains enough homology surrounding that site to allow the re-synthesis (by repair) of the restriction enzyme site on the targeting plasmid. Candidates that display a ULL are assumed to be homologous integration events and are subjected to further analysis. Unit length linears were seen for 6 of 21 epsilon-globin candidates analyzed and for 3 of 14 beta-globin candidates. No unit-length linears were observed in candidate clones isolated with any of the other targeting fragments used.

Figure 7:
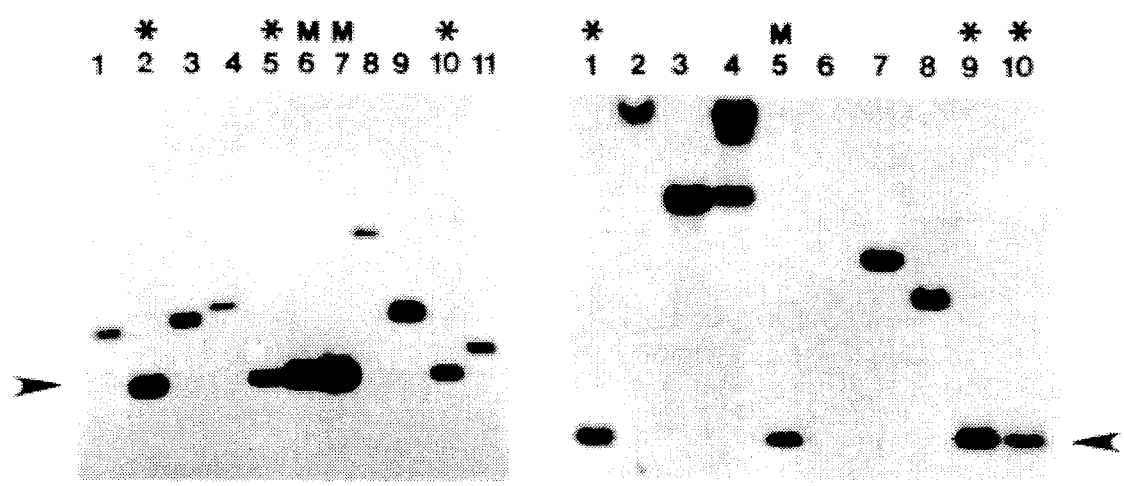
FIG. 7 is a restriction enzyme and Southern blot analysis of clones selected by targeting with human epsilon- and beta-globin sequences.

FIG. 7 is a restriction enzyme and Southern blot analysis of clones selected by targeting with human epsilon- and beta-globin sequences. In the left panel, DNA from nine clones selected as arg+ were digested with AvaII (the enzyme used to make the double-strand break in the beta-globin targeting sequence). In the right panel, DNA from nine clones selected as arg+ were digested with ApaI (the enzyme used to make the double-strand break in the epsilon-globin targeting sequence). The asterisks identify clones correctly selected by homologous recombination. The lanes marked M were loaded with purified beta-globin targeting plasmid digested with AvaII (left panel), or purified epsilon-globin targeting plasmid digested with ApaI (right panel). The size of this marker fragment is identical to the size predicted for correctly targeted events. The arrowheads indicate the fragment size predicted for correctly targeted events, 5.6 kb in the left panel and 6.2 kb in the right panel. Hybridization was with $^{32}P$ labeled ARG4 DNA.

Three each of the beta- and epsilon-globin positives were further analyzed by CHEF gel electrophoresis (Chu, G., Vollrath, D., and David, R. W. *Science*, 234:1582–1585 (1986)), and restriction enzyme and Southern hybridization analysis, probing with epsilon- or beta-globin DNA as appropriate. This analysis demonstrated that all six YACs are identical and carry both beta- and epsilon-globin DNA, as would be expected since these two genes lie only 40 kb apart on human chromosome 11. In all six YACs the ARG4 DNA has integrated onto a YAC of 190 kb and the p184DLARG constructs have integrated as predicted into the homologous DNA within the globin locus.

Homologous recombination has been successfully used to isolate unique genes from a DNA YAC library. The YACs isolated encompass the entire beta-globin locus from at least 16 kb 5' of the epsilon gene down to the beta globin gene, along with about 130 kb of flanking DNA. In addition, a similar selection protocol performed with the same DNA YAC library resulted in the isolation of YACs from the β-globin locus after the library had been stored at −70° C. for over fourteen months. It is thus disclosed here, for the first time, that it is possible to isolate clones from a human DNA YAC library by homologous-recombination selection.

EXAMPLE II

SELECTION BY HOMOLOGOUS-RECOMBINATION OF A DNA CLONE FROM A DNA YAC LIBRARY USING ONE-STEP GENE DISRUPTION

The method of one-step gene disruption (Rothstein, R. J., *Methods in Enzymology*, 101:202–211, Academic Press, New York, 1983) can be adapted for use in the selection of clones from DNA libraries by homologous recombination. In this embodiment, a selectable marker is inserted into the targeting sequence. The targeting sequence, with the embedded selectable marker, is subsequently isolated as a single linear fragment (as diagrammed in FIG. 3) and transformed into the pooled DNA YAC library, as described in Example I. Correctly targeted clones arising as a result of homologous recombination between the targeting molecule and specific DNA clones within the library will carry a single copy of the targeting sequence that is disrupted by the presence of the selectable marker, and will migrate at a specific and predictable position after restriction enzyme digestion and Southern blot analysis, using either ARG4 or the targeting sequence as a radiolabeled probe. This is in contrast to the process described in Example I, in which the correctly targeted DNA clones have two uninterrupted copies of the targeting sequence flanking the selectable marker.

FIG. 3 illustrates the selection by homologous recombination of a DNA clone from a DNA YAC library using one-step gene disruption. The thin line represents an insert of DNA in the form of a yeast artificial chromosome (YAC). The solid box is the DNA fragment, a sequence of DNA constituting a portion of a DNA YAC clone found in the library that is homologous to the targeting sequence. In the diagram, the targeting sequence (solid boxes) has been modified by the insertion of the yeast ARG4 gene (open box). The remaining portions of the DNA YAC are comprised of the YAC vector arms: the thick lines represent plasmid sequences for replication and selection in bacteria. The shaded boxes represent genetic markers used for selection in yeast (yeast selectable markers URA3 and TRP1). The solid arrowheads and circle represent telomeres (TEL) and a centromere/yeast replication origin (CEN/ARS), respectively. FIG. 3a depicts the targeting molecule aligning with the target sequence on the DNA YAC. FIG. 3b depicts the product of homologous recombination between the targeting and target sequences, with the targeting sequence having replaced the target sequence.

As a specific example of this embodiment of the basic concept, the 1.9 kb (HindIII) 5' epsilon-globin fragment (see Example I) is subcloned into the HindIII site of pUC18 (ATCC #37253). The resulting plasmid is digested with ApaI, dropping out a 0.26 kb ApaI fragment from the central portion of the 5' epsilon-globin insert. The 3' ApaI overhangs are made blunt with T4 DNA polymerase, and the resulting material is ligated to the purified ARG4 2.0 kb HpaI fragment (Beacham, I. R., *Gene*, 29:271–179, 1984). The resulting plasmid, with ARG4 disrupting the 5'epsilon-globin sequence, is digested with HindIII and transformed into the DNA YAC library, as described in Example I. The specific example presented results in the replacement of 0.26 kb of the 5' epsilon-globin DNA with the ARG4 sequence, since ApaI is not unique in the targeting sequence. For enzymes that are unique in the targeting sequence, however, the result will be a simple insertion.

EXAMPLE III

HOMOLOGOUS-RECOMBINATION CHROMOSOME WALKING UTILIZING TWO YAC LIBRARIES

A. Construction of Yeast Artificial Chromosome (YAC) Libraries

A.1) *Saccharomyces Cerevisiae*

Host Strain Construction

The construction of a strain of *S. cerevisiae* carrying chromosomal deletions of each of the four genes used as selectable markers on the four YAC vectors described can be carried out as follows:

A.1.a) Deletion of ARG4:

The internal 2.0 kb HpaI fragment carrying the entire structural gene and regulatory elements for the yeast argininosuccinate lyase gene (ARG4) is deleted from a plasmid consisting of the 11 kb BamHI fragment isolated from p(SPO13)2 (Wang, H-T., et al., *Molecular and Cellular Biology*, 7:1425–1435, 1987) inserted into the BamHI site of pUC19 (ATCC #37254), by digestion with HpaI and relegation of the DNA under dilute conditions (1 µg/ml). The resulting plasmid is digested with BamHI and introduced into an *S. cerevisiae* strain carrying the wild-type alleles for ARG4, TRP1, URA3, and LEU2, and carrying any non-reverting his3⁻ allele. The transformation is carried out in conjunction with any plasmid carrying yeast CEN and ARS elements, and the yeast HIS3 gene, using standard co-transformation conditions (Ausubel, F. M. et al., *Current Protocols in Molecular Biology*, Chapter 13, Greene Publishing Associates and Wiley-Interscience, New York, 1989). A useful plasmid for this purpose can readily be constructed by subcloning the 1.7 kb BamHI fragment from pRB15 (ATCC #37062) into the BamHI site of YCp50 (ATCC #37419). His⁺ cells are screened for arginine auxotrophy by replica plating onto CM -arginine plates. His⁺ arg⁻ cells are grown in the absence of selection for HIS3, and single colonies are isolated and screened for histidine auxotrophs. DNA from his⁻ arg⁻ colonies is prepared and analyzed by restriction enzyme and Southern blot analysis to identify transformants carrying the ARG4 deletion (arg4Δ). This protocol is used to generate strain MGD131-10c used in Example I above.

A.1.b) Deletion of TRP1:

In a yeast strain of opposite mating type as that used above, also carrying mutant alleles for LEU2 and URA3 (leu2⁻, ura3⁻), an identical procedure is carried out, but using a linear fragment of DNA carrying a deletion of the yeast gene for N-(5'-phosphoribosyl)-anthranilate isomerase (TRP1). This is accomplished by subcloning the BamHI-XhoI fragment from pBR322-Sc4120 (Stinchcomb, D. T., et al., *Journal of Molecular Biology*, 158:157–179, 1982) into BamHI-XhoI cut pGEM7, (Promega, Madison, Wis.) followed by deletion of the 1.2 kb EcoRI fragment containing TRP1 and ARS1. The resulting plasmid, pK2, is digested with BamHI and XhoI and co-transformed with a HIS3-CEN-ARS plasmid, like that described in A.1.a) above, selecting for histidine prototrophs, and following the strategy outlined in A.1.a.) above to identify cells carrying the TRP1 deletion (trp1Δ). These cells are mated with cells carrying arg4Δ, and diploids heterozygous for the two deletions are isolated. This strain, TD7-16d, is sporulated, subjected to tetrad analysis, and spores with appropriate phenotypes are analyzed by restriction enzyme and Southern blot analysis to identify a strain with both the arg4Δ and trp1Δ alleles (IV-16d used in Example I above). The genotype of TD7-16d is: a/α, arg4Δ/ARG4, LEU2/leu2-3,112, ura3-52/URA3, trp1-289/trp1Δ, ade2-101/ade2-101, cyh$^s$/cyh$^r$, (CYH2/cyh2), his3a1/his3Δ1

A.1.c) Deletion of LEU2 and URA3:

Strain TD7-16d is used as the recipient in additional co-transformation experiments, first with a linear DNA fragment carrying an internal deletion of the 1.3 kb HincII-AccI fragment corresponding to the yeast β-isopropylmalate dehydrogenase gene (LEU2), and subsequently with a linear fragment carrying an internal deletion of the 0.85 kb PstI-NsiI fragment corresponding to the yeast orotidine-5'-phosphate decarboxylase gene (URA3). The plasmids YEp13 (ATCC #37115; Broach, J. R., et al., *Gene*, 8:121, 1979) and YIp30 (ATCC #37109; Botstein, D., et al. Gene, 8:17–24, 1979) are used as sources for constructing deletion derivatives of the LEU2 and URA3 genes, respectively. A diploid that is heterozygous for all four deletions is sporulated, subject to tetrad analysis, and screened for haploid colonies that have the minimal genotype MATa arg4Δ trp1Δ leu2Δ ura3Δ. This is the recipient strain for constructing Libraries 1 and 2. (See FIG. 4.)

A.2) Construction of Yeast Artificial Chromosome (YAC) Vectors:

The construction of an artificial chromosome requires that sequences capable of stabilizing the ends of linear DNA molecules (telomeres or TEL elements) be ligated to each end of the DNA chosen for cloning. In addition, each end needs to carry: 1) a yeast gene that can be used for genetic selection in the initial construction of the library and for subsequent use as a selectable marker for use in selecting clones out of a library by homologous recombination, and 2) sequences that allow replication in *E. coli* and confer antibiotic resistance in *E. coli* (selectable markers). Each end should also carry a sequence that functions as an initiation site for DNA replication (an ARS element). Finally, one and only one, of the two ends must carry a sequence that functions as a centromere in yeast (a CEN element).

To ensure that each linear DNA molecule transformed into yeast has two different ends (only one of which caries a CEN element), to facilitate the identification and recovery of each end uniquely, and to generate the two YAC libraries (Library 1 and Library 2), a total of four different ends are needed, utilizing four different yeast genes and four different antibiotic resistance markers. All of the various elements described above are ligated together in specific arrangements to generate yeast artificial chromosome vectors which can be propagated and manipulated in *E. coli*. To minimize the possibility of homologous recombination between the ends of artificial chromosomes in Library 2 and targeting plasmids isolated from Library 1, the bacterial origins of replication on the vectors used in the construction of each individual library are from different sources. So that the final vectors are compact, easy to manipulate, and unlikely to rearrange by virtue of the duplicated bacterial origins of replication, each of the four ends is maintained as a different plasmid in bacteria, in contrast to the invention described in U.S. Pat. No. 4,889,806.

A.2.a) Construction of a CEN-ARS Element

The PstI site of pUC19 (ATCC #37254) is removed by blunting with T4 DNA polymerase and recircularization with T4 DNA ligase. The resulting plasmid (pCU19/Pst⁻ is cut with EcoRI and SmaI and the 3.1 kb EcoRI-SmaI fragment from A75p9 (carries ARS1, TRP1, and CEN3; Murray, A. W. and Szostak, J. W., *Nature*, 305:189–193, 1983) is inserted. The resulting plasmid (pT10H) is cut with StuI and BamHI, removing the TRP1 gene and all CEN3 sequences. The StuI-BamHI fragment carrying the pUC19/Pst⁻ backbone and ARS1 is gel purified and ligated to a 382 bp Sau3A-ScaI fragment carrying CEN3 isolated from A75p9 (Murray, A. W. and Szostak, J. W., *Nature*, 305:189–193, 1983). The resulting plasmid (pT12H) carries ARS1 sequences from positions 829–1453 in the published TRP1 sequence (Tschumper G. and J. Carbon, *Gene*, 10:157–166, 1980) fused to CEN3 sequences 1–382 (Bloom, K. S. and J. Carbon, *Cell*, 29:305–317, 1982), with both fragments inserted between the EcoRI and BamHI sites of the pUC19/Pst⁻ polylinker.

A.2.b) Construction of a YAC ARM VECTOR pTK-ENDA2

Figure 6A:
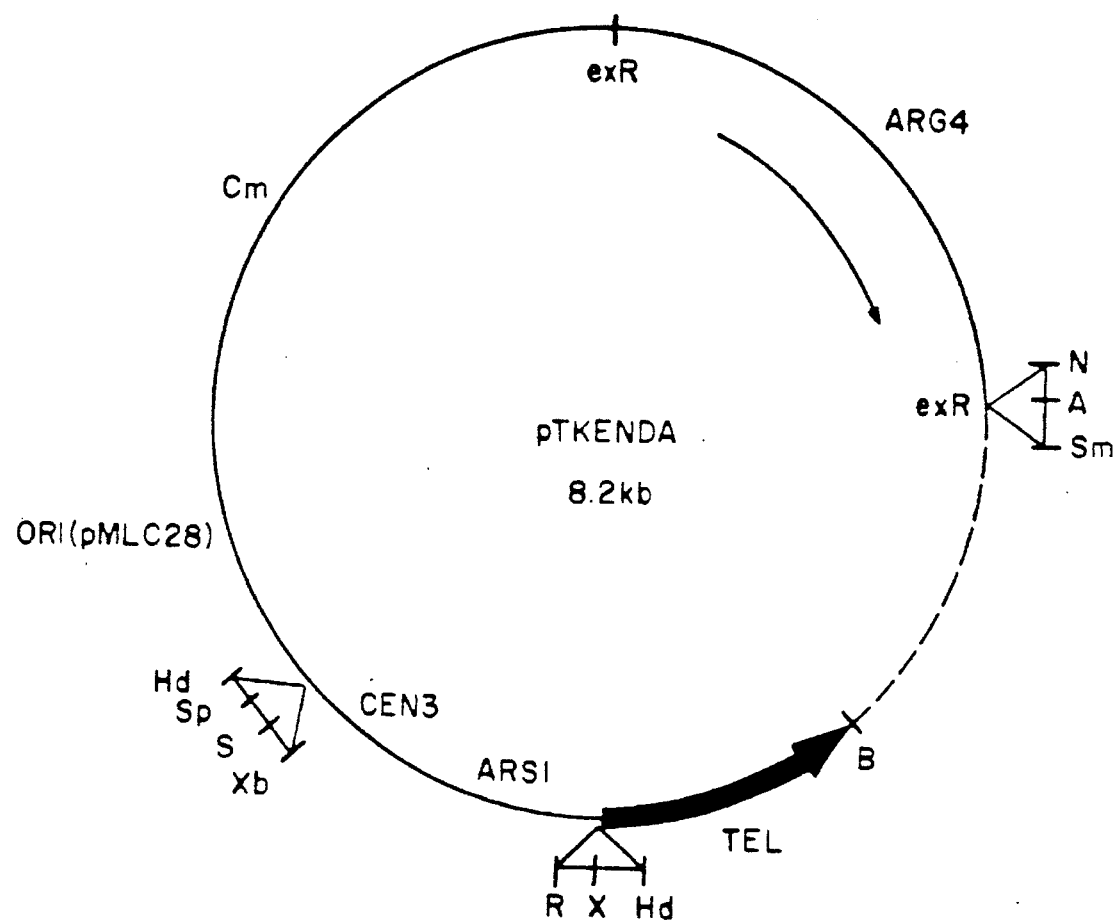
FIG. 6a is a plasmid map of pTKENDA.

The Sau96 site of pMLC28 (pSDC12 with pUC19 polylinker; Levinson, A., et al. *J. Mol. Appl. Gen.*, 2:507–517, 1984) is removed by blunting with T4 DNA polymerase and recircularization with T4 DNA ligase. The resulting plasmid (pMLC28/Sau⁻) is digested with EcoRI and BamHI, and annealed with oligonucleotides 1 and 2 (FIG. 8a), and treated sequentially with T4 DNA ligase, T4 DNA polymerase, and T4 DNA ligase. The treated molecules are transformed into *E. coli*, and chloramphenicol resistant transformants are screened for the presence of an ApaI site expected to be found in recombinant plasmids carrying the oligonucleotides. Plasmids which also regenerate the EcoRI and BamHI sites are subjected to dideoxy DNA sequence analysis. One plasmid with the correct sequence (pMLC28/SL) is digested with EcoRI, blunted with T4 DNA polymerase, and ligated to the 2.0 kb HpaI fragment carrying the yeast ARG4 gene. (Beacham, I. R., et al., *Gene*, 29:271–279, 1984). The resulting plasmid with a single insert of the HpaI fragment (pT20) is cut with BamHI and HindIII, and mixed with a purified 0.7 kb BamHI-EcoRI TEL fragment and the 1.0 kb EcoRI-HindIII fragment containing ARS1 and CEN3 from pT12H (Section A.2.a.). Transformants resulting from this three way ligation are screened by restriction enzyme analysis. The correct plasmid (pT21) is digested with SmaI and BamHI, and ligated to a 1.8 kb SmaI-BamHI fragment derived from *E. coli*. The resulting plasmid is named pTKENDA. FIG. 6a illustrates the plasmid map of pTKENDA, with relevant features and restriction sites. N: NsiI; A: ApaI; Sm: SmaI; B: BamHI; Hd: HindIII; X: XhoI; R: EcoRI; Xb: XbaI; S: SalI (HindII); Sp: SphI; ARG4: yeast ARG4 gene; Cm: chloramphenicol resistance gene; ORI(pMLC28): pMLC28 origin of replication; CEN3, ARS1: yeast CEN3 (centromere) and ARS1 (replication origin), respectively; TEL: sequence that seeds telomere formation in yeast; exR: former EcoRI sites; dashed line: stuffer DNA fragment derived from *E. coli*. The arrow indicates the direction of ARG4 transcription.

The CEN3-ARS1 element used in pTKENDA is not the preferred sequence to use for constructing DNA YAC libraries. To convert pTKENDA to the more preferred derivative, pTKENDA is digested with XbaI and treated with the Klenow fragment of *E. coli* DNA polymerase to create a blunt end. This DNA is then cut with BamHI, dropping out the CEN3-ARS1 element originally derived from pT12H (section A.2.a) and the TEL sequence. The 6.5 kb fragment (referred to as fragment A in this modification) carrying ARG4, the *E. coli* DNA stuffer fragment and the chloramphenicol resistance gene is gel purified. Separately, pTKENDA is digested with HindIII and BamHI and the 0.7 kb TEL fragment (referred to as fragment B in this modification) is gel purified.

Plasmid YCp19 (ATCC #37364) is digested with HindIII, PvuII, and XbaI and the 2.6 kb HindIII-PvuII fragment carrying CEN4 and ARS1 is gel purified (referred to as fragment C in this modification). Fragments A, B, and C are ligated together, transformed into *E. coli*, and chloramphenicol resistant colonies are screened for plasmids with a single copy of fragments A, B, and C. The resulting plasmid is pTKENDA2.

A.2.e) Construction of a YAC ARM VECTOR pTKENDB

The 827 bp EcoRI-PstI fragment from YRp7 (ATCC #37060), carrying the yeast TRP1 gene, is blunted with T4 DNA polymerase and ligated to HincII cut pUC19 (ATCC #37254). One plasmid, pT32H, is isolated in which the direction of transcription of the TRP1 gene is directed away from the EcoRI site of the pUC19 polylinker. This plasmid is cut with EcoRI and BamHI, annealed with Oligos 3 and 4 (FIG. 8a), and treated sequentially with T4 DNA ligase, T4 DNA polymerase, and T4 DNA ligase. The treated molecules are transformed into *E. coli*, and ampicillin resistant transformants are screened for the presence of an ApaI site expected to be found in recombinant plasmids carrying the oligonucleotides. Plasmids which also regenerated the EcoRI site are subjected to dideoxy DNA sequence analysis. One plasmid with the correct sequence (pT32LH) is purified for further use.

Figure 6B:
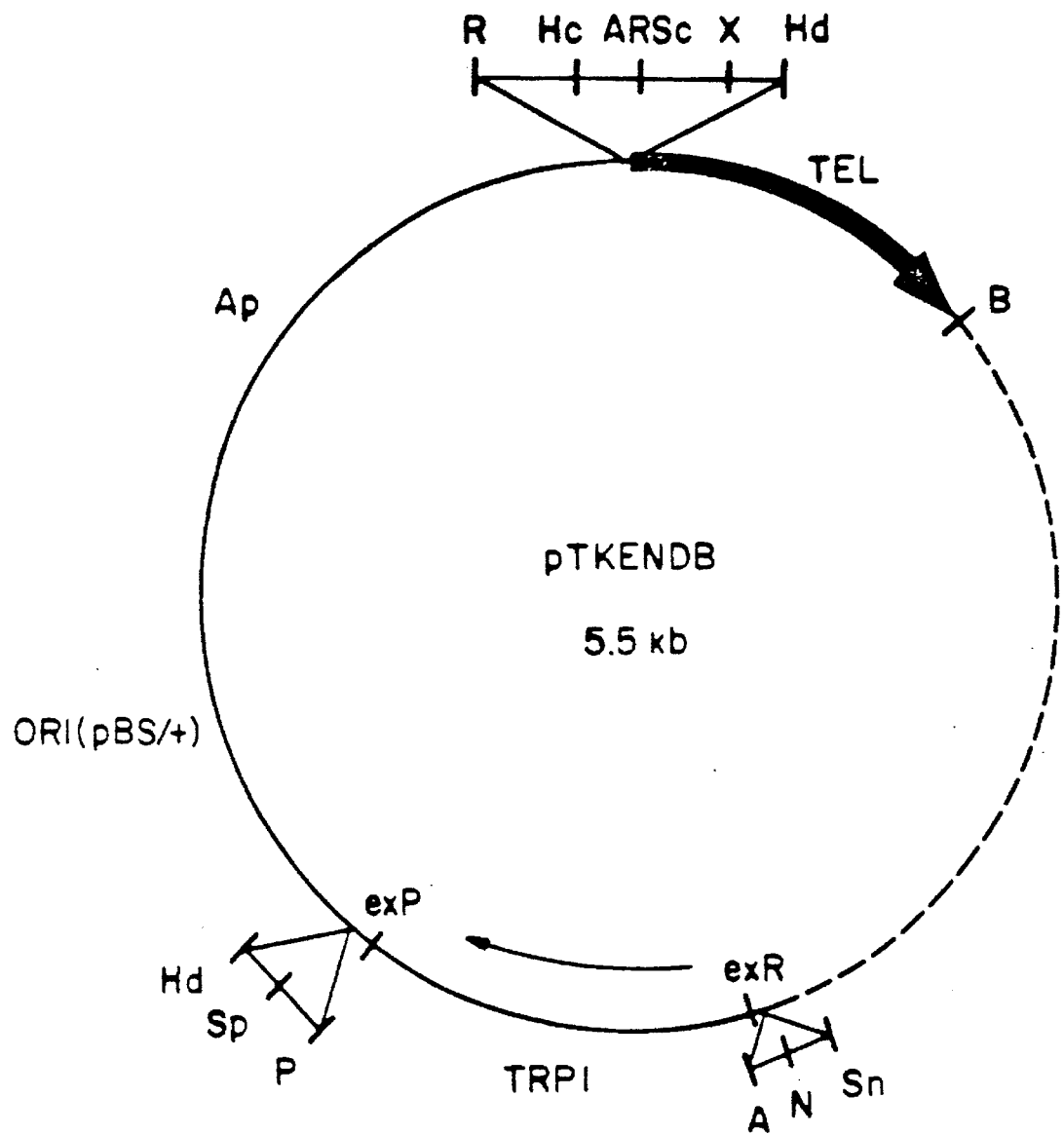
FIG. 6b is a plasmid map of pTKENDB.

Plasmid pBS/+ (Stratagene Cloning Systems, LaJolla, Calif.) is cut with AatII and EcoRI and blunted with T4 DNA polymerase to delete the LacZ gene. The resulting molecules are circularized with T4 DNA ligase and ampicillin-resistant *E. coli* transformants are analyzed for the correct deletion derivative which regenerates the EcoRI site. One plasmid (pBSΔ) is cut with EcoRI and PstI (both of which cut within the pBS/+ polylinker), and ligated to the 0.85 kb TRP1 EcoRI-PstI fragment from pT32LH. Ampicillin-resistant transformants from this ligation are screened by restriction enzyme analysis for molecules with the correct structure (pT32BH). pT32BH is then cut with BamHI-XhoI TEL fragment from pTKENDA, and transformants are screened by restriction (Section A.2.b.) enzyme analysis for molecules with a single insert of the TEL fragment. This plasmid, pT33H, is cut with SphI, blunted by treatment with T4 DNA polymerase and recircularized with T4 DNA ligase. The resulting plasmid is pT34H. pT34H is digested with SnaBI and BamHI, and ligated to the 1.2 kb SnaBI-BamHI fragment from plasmid pBR:βa (ATCC #39698). The resulting plasmid is designated pTKENDB. FIG. 6b is a plasmid map of pTKENDB, with relevant features and restriction enzyme recognition sites: N: NsiI; A: ApaI; Sn: SnaBI; B: BamHI; Hd: HindIII; X: XhoI; R: EcoRI; Xb: XbaI; Hc: HincII; Sp: SphI; P: PstI; TRP1: yeast TRP1 gene; Ap: ampicillin resistance gene; ORI(pBS/+): pBS/+ origin of replication; ARSc: consensus ARS sequence (TAAACATAAAA SEQ ID NO:26 ; Broach J. et al., *Cold Spring Harbor Symp. Quant. Biol.* 47:1165 (1983)). TEL: sequence that seeds telomere formation in yeast; exR, former EcoRI site; exP; former PstI site; dashed line: stuffer DNA fragment derived from human beta-globin DNA. The arrow indicates the direction of TRP1 transcription.

A.2.d) Construction of a YAC Arm Vector pTKENDC

The 622 bp SalI-HindIII fragment from pACYC184 (ATCC #37033; Chang, A. C. Y. and Cohen, S. N. *Journal of Bacteriology,* 134:1141–1156, 1978) is subcloned into SalI-HindIII cut pBS/– (Stratagene Cloning Systems, LaJolla, Calif.) to generate pT40H. The host strain XL1-Blue (Stratagene Cloning Systems, LaJolla, Calif.) is infected with wild-type M13 (Bio-Rad Laboratories, Rockville Centre, N.Y.) and a mixture of wild-type and pT40H phage particles are isolated. Cells from the dut⁻ung⁻ *E. coli* strain CJ236 (Bio-Rad Laboratories, Rockville Centre, N.Y.) are infected with this mixture of phage, and a mixture of pT40H and M13 single-stranded DNA is isolated. Oligo 13 (FIG. 8c) is used essentially as described by Kunkel (Kunkel, T. A. *Proceedings of the National Academy of Sciences U.S.A.,* 82:488–492, 1985) to introduce a C to T substitution at the XhoII site corresponding to position 1870 of pACYC184, to generate pT40/X⁻H. The 622 bp SalI-HindIII fragment from pT40/X⁻H is isolated and ligated to the 3.6 kb SalI-HindIII fragment of pACYC184 purified by gel electrophoresis. The resulting plasmid (pT41H) is cut with XmnI and StyI, blunted by treatment with T4 DNA polymerase, ligated to EcoRI linkers (CGGAATTCCG SEQ ID NO.:27), and cut with EcoRI to generate EcoRI overhanging ends. The 2237 bp EcoRI-linked XmnI-StyI fragment is purified by gel electrophoresis.

BamHI linkers are added on to the 1.1 kb HindIII fragment from YIp30 (ATCC #37109) that carries the URA3 gene. This fragment is inserted into the BamHI site of pBS/+ (Stratagene Cloning Systems, LaJolla, Calif.), such that the orientation of URA3 transcription is directed away from the EcoRI site in the polylinker. The resulting plasmid is cut with HindIII, blunted with T4 DNA polymerase, and recircularized with T4 DNA ligase to remove the HindIII site of the polylinker. The resulting plasmid is cut with NsiI and SalI, blunted with T4 DNA polymerase, and recircularized with T4 DNA ligase to remove the NsiI, BamHI (3' side of URA3 only), XbaI, and SalI sites in the plasmid. The resulting plasmid is cut with EcoRI and BamHI and annealed with Oligos 5 and 6 shown in FIG. 8b. The mixture is treated with T4 DNA ligase, T4 DNA polymerase, and again with T4 DNA ligase, and transformed into bacteria. Ampicillin-resistant transformants are screened by restriction enzyme analysis for the presence of an ApaI site introduced with the polylinker, and plasmids that regenerate and EcoRI site are subject to dideoxy DNA sequencing to confirm the correct polylinker sequence. This plasmid is pURA3LH.

Figure 6C:
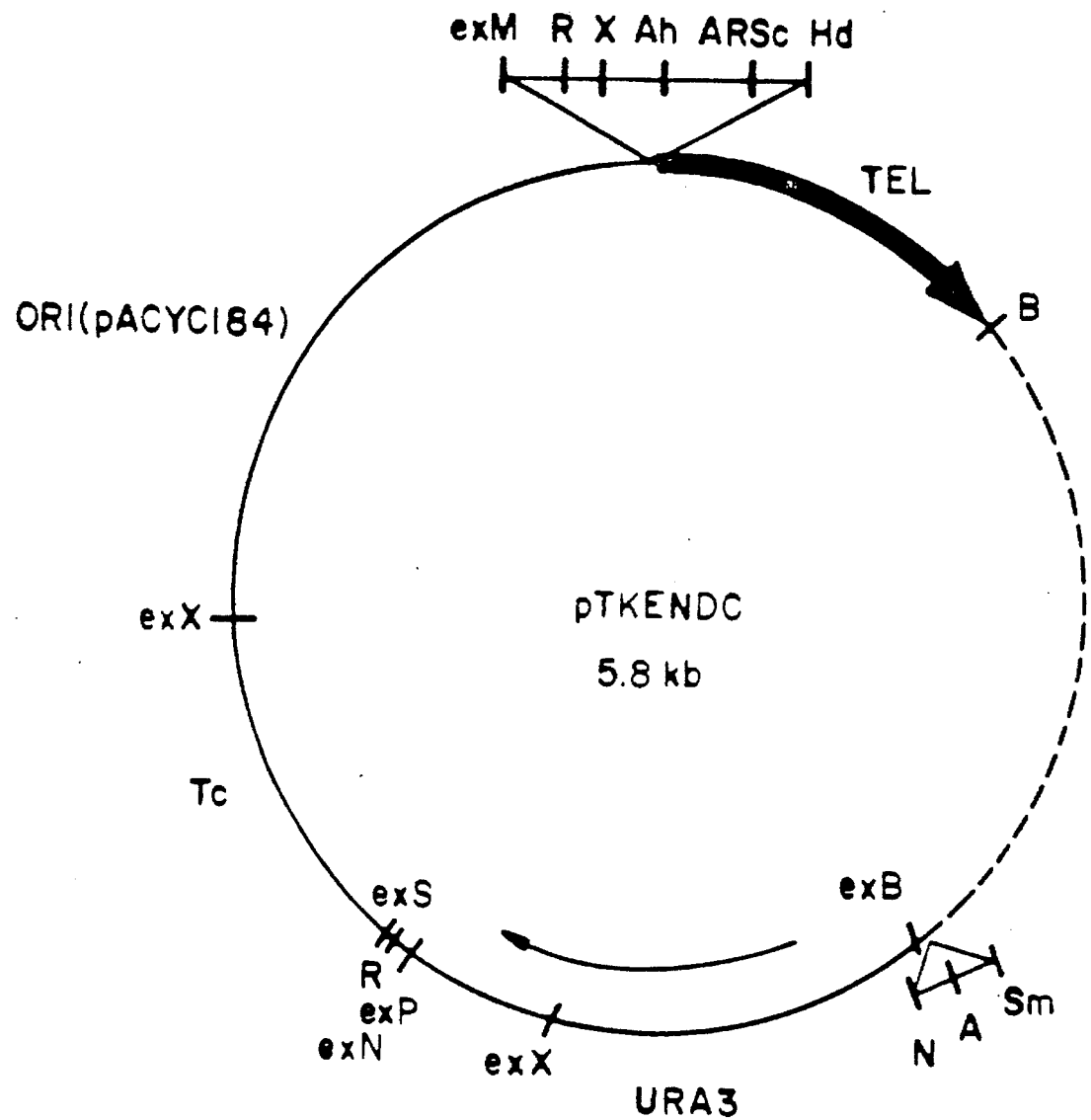
FIG. 6c is a plasmid map of pTKENDC.

The host strain XL1-Blue (Stratagene Cloning Systems, LaJolla, Calif.) is infected with wild-type M13 (Bio-Rad Laboratories, Rockville Centre, N.Y.) and a mixture of wild-type and pURA3LH phage particles is isolated. Cells from the dut⁻ung⁻ E. coli strain CJ236 (Bio-Rad Laboratories, Rockville Centre, N.Y.) are infected with this mixture of phage, and a mixture of pURA3LH and M13 signle-stranded DNA is isolated. Oligonucleotide 12 (FIG. 8c) is used essentially as described by Kunkel (Kunkel, T. A., Proceedings of the National Academy of Sciences (U.S.A.), 82:488–492, 1985) to introduce a base substitution at the XhoII site at position 906 in the published URA3 sequence (Rose M. Grisafi, et al., *Gene*, 29:113–114). The resulting plasmid, pURA3LHX⁻, is cut with EcoRI and BamHI, and ligated to the 0.7 kb EcoRI-BamHI TEL fragment from pTKENDA (Section A.2.b.). The resulting plasmid, pT42H, is cut to completion with EcoRI and partially with PstI, blunted with T4 DNA polymerase, ligated to EcoRI linkers (CGGAATTCCG SEQ ID NO.:27), and cut with EcoRI to generate EcoRI overhanging ends. The 1.7 kb EcoRI-linked fragment is purified by gel electrophoresis and ligated to the EcoRI-linked fragment from pT41H purified above. Tetracycline resistant transformants are analyzed by restriction enzyme analysis for molecules with a single copy of each fragment in either orientation. This plasmid is digested with BamHI and SmaI and the same 1.8 kb stuffer fragment derived from *E. coli* used in the construction of pTKENDA is inserted. The resulting plasmid is designated pTKENDC. FIG. 6c is a plasmid map of pTKENDC, with relevant features and restriction enzyme recognition sites. N: NsiI; A: ApaI; Sm: SmaI; B: BamHI; Hd: HindIII; X: XhoII; R: EcoRI; Ah: AhaIII; URA3: yeast URA3 gene; Tc: tetracycline resistance gene; ORI(pACYC184): PACYC184 origin of replication; ARSc: consensus ARS sequence (TAAACATAAAA SEQ ID NO.:26; Broach, J. et al., (1983) *Cold Spring Harbor Symp. Quant. Biol.*, 47:1165). TEL: sequence that seeds telomere formation in yeast; exS, exM, exN, exP, exB, exX: former StyI, XmnI, NsiI, PstI, BamHI, and XhoII sites, respectively; dashed line: stuffer DNA fragment derived from *E. coli*. The arrow indicates the direction of URA3 transcription.

A.2.e) Construction of a YAC Arm Vector pTKENDD pACYC177 (ATCC #37031; Chang, A. C. Y. and Cohen, S. N. *Journal of Bacteriology*, 134:1141–1156, 1978) is cut with Sau96, blunted by treatment with T4 DNA polymerase, and the 1.2 kb fragment carrying the kanamycin resistance gene is isolated by gel electrophoresis. This fragment is ligated to HincII cut pBS/+ (Stratagene Cloning Systems, LaJolla, Calif.) and chloramphenicol and kanamycin resistant clones are analyzed by gel electrophoresis for recombinants with the kanamycin gene inserted such that the direction of transcription is directed away from the EcoRI site in the pBS/+ polylinker. The blunt-ending of the Sau96 sites and subsequent ligation to HincII cleaved pBS/+ results in SalI sites at the left and right junctions. This plasmid is pT50H. To remove one of the two inverted repeats flanking the kanamycin resistance gene (the 5' inverted repeat relative to the direction of transcription), pT50H is cleaved with SalI and DraIII and the 1.08 kb fragment containing the kanamycin resistance gene is purified, blunt-ended by treatment with T4 DNA polymerase, and ligated to HincII digested pBS/+. The resulting plasmid, with transcription of the kanamycin resistance gene directed away from the EcoRI site in the pBS/+ polylinker, is pT50ΔSD. pT50ΔSD is introduced into the host strain XL1-Blue (Stratagene Cloning Systems, LaJolla, Calif.), and subsequently infected with wild-type M13 (Bio-Rad Laboratories, Rockville Centre, N.Y.) and a mixture of wild-type and pT50ΔSD phage particles are isolated. Cells from the dut⁻ung⁻ E. coli strain CJ236 (Bio-Rad Laboratories, Rockville Centre, N.Y.) are infected with this mixture of phage, and a mixture of pT50ΔSD and M13 single-stranded DNA is isolated. Oligonucleotides 14, 15 and 16 (FIG. 8c) are used essentially as described by Kunkel (Kunkel, T. A.,) *Proceedings of the National Academy of Sciences U.S.A.*, 82:488–92, 1985) to introduce base substitutions at two NsiI sites (positions 2203 and 2469 of the published pACYC177 sequence) and at an XhoII site at position 2602 of pACYC177. The resulting plasmid, pT50HX is cut with EcoRI and SphI, blunted with T4 DNA polymerase, and circularized with T4 DNA ligase, (regenerating the EcoRI site). The resulting DNA preparation is then cut with XbaI. This fragment is ligated to the 882 base pair AccI-XhoII fragment of pACYC177 (which has been blunted with T4 DNA polymerase, ligated with XbaI linkers (GCTCTAGAGC SEQ ID NO.:28), and treated with XbaI to generate XbaI overhangs) carrying the plasmid origin of replication, to generate plasmid pT51H (either orientation will suffice).

Figure 6D:
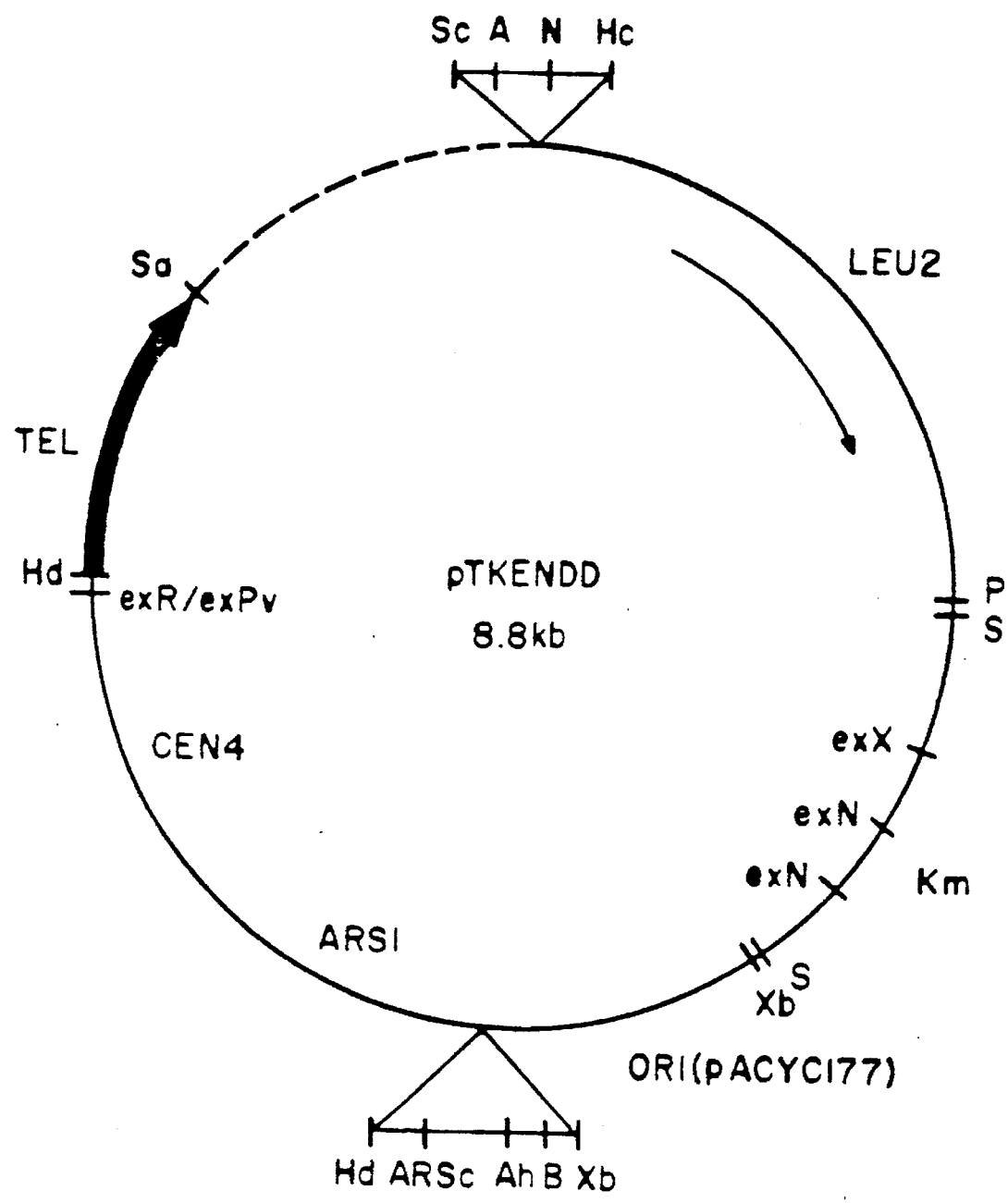
FIG. 6d is a plasmid map of pTKENDD.

Plasmid pT52H is constructed by cutting plasmid YIp33 (ATCC #37064) with HpaI and AccI to release a 1.6 kb fragment containing the yeast LEU2 gene (Andreadis, A., et al., *Cell*, 31:319–325, 1982). This fragment is blunted with T4 DNA polymerase and ligated to pUC18 (ATCC #37253) cut with HincII. The resulting plasmid is cut with BamHI and XbaI, and annealed with oligonucleotides 7 and 8 (FIG. 8b). The mixture is treated with T4 DNA ligase, T4 DNA polymerase, and again with T4 DNA ligase, and transformed into bacteria. Ampicillin resistant transformants are screened by restriction enzyme analysis for the presence of an ApaI site introduced with the polylinker and plasmids that regenerate a BamHI site are subject to dideoxy DNA sequencing to confirm the correct polylinker sequence. The resulting plasmid is pT52LH. pT52LH is digested with BamHI and PstI, and the gel purified 1.6 kb fragment is ligated to pT51H cut with BamHI and PstI. The resulting plasmid, pT53H, is digested with ScaI and BglII, and ligated to the double-stranded oligonucleotide shown in FIG. 8c (oligonucleotides 9A and 9B). The resulting plasmid (pT53HL) is partially digested with HindIII, followed by complete digestion with BglII and the digestion product corresponding in size to linearized pT53HL (approximately 3.7 kb) is purified. This species represents cleavage at the adjacent HindIII and BglII sites introduced via Oligonucleotides 7 and 8 (FIG. 8b). Plasmid pTKENDA (Section A.2.b and ATCC accession number 40833) is digested with EcoRI and treated with the Klenow fragment of *E. coli* DNA polymerase to generate a blunt end. This DNA is then digested with BamHI and the 0.7 kb TEL fragment is gel purified. Plasmid YCp19 (ATCC #37364) is digested with HindIII, PvuII, and PvuI and the 2.6 kb HindIII-PvuII fragment carrying CEN4 and ARS1 is gel purified. The purified CEN4-ARS1 and TEL fragments are ligated to BglII-HindIII digested pT53HL and transformed in *E. coli*. Kanamycin resistant transformants are screened for plasmids with a single copy each of the CEN4-ARS1, TEL, and T53HL fragments. The resulting plasmid is pT54H. pT54H is digested with PvuII and SacI, and ligated to the 1.5 kb SacI- PvuII fragment lying between positions 25,881–27,414 on the bacteriophage Lambda (New England Biolabs, Beverly, Mass.) map. The resulting plasmid is pTKENDD. FIG. 6d is a plasmid map of pTKENDD with relevant features and restriction enzyme recognition sites. N: NsiI; A: ApaI; B: BamHI; Hc: HincIII; Pv: PvuII; P: PstI, S. SalI(HincII); Hd: HindIII; X: XhoII; Xb: XbaI; Sa: SacI; Ah: AhaIII; LEU2: yeast LEU2 gene; Km: Kanamycin resistance gene: ORI (pACYC177): pACYC177 origin of replication; ARSc: consensus ARS sequence (TAAACATAAAA SEQ ID NO.:26; Broach, J. et al., (1983) *Cold Spring Harbor Symp. Quant. Biol.* 47:1165). CEN4/ARS1: CEN4/ARS1 fragment from YCp19 (see text); TEL: sequence that seeds telomere formation in yeast; exR, exPv, exN, exX: former EcoRI, PvuII, NsiI and XhoII sites, respectively; dashed line: stuffer DNA fragment derived form bacteriophage Lambda. The arrow indicates the direction of LEU2 transcription.

A.3) Construction of Yeast Artificial Chromosome (YAC) Libraries

DNA from human white blood cells is prepared and partially digested with restriction endonucleases, essentially as described (D.Burke, Ph.D. thesis, Washington Univ., St. Louis, Mo. (1988)). DNA (with a desired average size of greater than 1.5 megabases) is partially digested with ApaI, NsiI, or any enzyme that leaves a blunt end. To construct Library 1, plasmids pTKENDA2 and pTKENDB are used. pTKENDA2 is cleaved with BamHI and either ApaI, NsiI, or SmaI to release the stuffer fragment. pTKENDB is cleaved with BamHI and either ApaI, NsiI, or SnaBI to release the stuffer fragment. For the construction of Library 2, plasmids pTKENDC and pTKENDD are used. pTKENDC is digested with BamHI and either ApaI, NsiI, or SmaI to release the stuffer fragment. pTKENDD is digested with SacI and either ApaI, NsiI, or PvuII to release the stuffer fragment.

Each vector is treated with calf intestine alkaline phosphatase under conditions recommended by the supplier and purified by phenol extraction and ethanol precipitation. For each library, 50 μg of human DNA and 25 μg of each vector in each pair (pTKENDA2-pTKENDB or pTKENDC-pTKENDD) are mixed and ligated using T4 DNA ligase for 2 days at 12° C., in a ligation buffer recommended by the enzyme supplier. The ligated DNA is size fractionated by Field Inversion Gel Electrophoresis (Carle et al., *Science*, 232; pp 65–68, 1986) in low-gelling temperature agarose (FMC Corp., Rockland, Me.), or CHEF gel electrophoresis (Chu et al., 1986 op cit) and the portion of the gel containing DNA of 250–450 kb is excised and equilibrated with TE buffer+45 mM NaCl.

A.3.b) Transformation of Yeast Spheroplasts with DNA Ligated to YAC Vector Arms and Selection of Yeast Cells carrying Artificial Chromosomes DNA prepared as described in section A.3.a. can be used to transform a haploid *S. cerevisiae* strain carrying chromosomal deletions for ARC4, TRP1, URA3, and LEU2 to arginine and tryptophan prototrophy using human DNA ligated to pTKENDA2 and pTKENDB, essentially as described by Burgers and Percival (1987), with the following modifications: 10–20 μl of the low-melt agarose carrying the DNA is melted at 68° C. for 3 to 5 minutes. Carrier DNA (sheared salmon sperm or calf thymus DNA) is added to the cells to a final concentration of 30–40 μg/ml immediately before 200 μl of cells is added to the melted gel slice.

For plating and selection of yeast cells carrying artificial chromosomes, transformed cells are mixed with top agar (1M sorbitol, 2% dextrose, 0.5% ammonium sulfate, 0.17% yeast nitrogen base (Difco), 2.5% Bacto-agar (Difco), 0.005% adenine sulfate, and supplemented with uracil and all of the amino acids listed in Table 13.1.1 of Ausubel et al. (Ausubel et al., *Current Protocols in Molecular Biology*, Greene Publishing Associates and Wiley-Interscience, New York, 1987) at the listed concentrations, but omitting arginine and tryptophan for selection. The mixture of cells and top agar is poured onto the surface of agar plates made identically to the top agar except that the final concentration of agar is 2% in the plates. Plates are incubated at 30° C. for 5–7 days.

To construct Library 2, human DNA ligated to pTKENDC and pTKENDD are used to transform the same *S. cerevisiae* strain to uracil and leucine prototropy. Top agar and plates are prepared as described above, but lacking only uracil and leucine.

A.3.c) Pooling of Clones

Yeast colonies growing on plates selective for markers present on artificial chromosomes are transferred using sterile toothpicks into individual wells of 96-well microtiter plates filled with 200 μl of selective media. Plates are incubated with shaking at room temperature for 2 days and stored at 4° C. for up to one week. A fully representative YAC library of the human genome should be comprised of 50,000 independent clones, assuming an average clone size of 300 kb. This number of clones would fill 521 microtiter plates and is stored as 10 separate subpools. When approximately 52 plates are filled, 100 μl from each well is withdrawn, pooled, and thoroughly mixed with an equal volume (approximately 500 ml) of 30% sterile glycerol. The cell density of the cells in glycerol should be about $2.5 \times 10^7$ cell/ml, and can be adjusted to this density by counting cells prior to glycerol addition. The pooled cells are then aliquoted into microcentrifuge tubes in volumes of 0.1 to 1 ml, set on dry ice to quick freeze, and stored at −70° C. This is repeated for each of the 10 separate subpools.

B.) Transformation of Pooled Library 1 with a Targeting Plasmid and Selection of Specific Artificial Chromosome Clones The isolation of DNA YACs by homologous recombination is illustrated in Steps 1 and 2 of FIG. 4.

B.1.) Construction of the Targeting Plasmid

The desired fragments of human DNA (the targeting sequences), previously identified as being unique or at low copy number in the human genome are substituted for the TEL and stuffer domains of pTKENDC. 50 μg of the resulting subclones are prepared and digested to completion with a restriction endonuclease which generates a linear molecule harboring a double-strand break or gap in the targeting sequence, in such a manner that at least 150 base pairs, but possibly less, of targeting DNA remains on either side of the break or gap, and the pTKENDC vector backbone is intact and contiguous with the targeting DNA. The digested DNA is purified by phenol extraction and ethanol precipitation and resuspended in 20 μl.

B.2.) Transformation of YAC Library 1 with the Targeting Plasmid and Selection of Clones Homogolous to the Targeting Sequence 0.1 ml of each of the 10 subpools are combined in 100 ml CM -arg, trp selective media supplemented to 0.05X YPD. Cells are grown overnight with vigorous shaking at 30C to a density of $2 \times 10^7$ cells/ml. Cells are prepared for transformation by the lithium acetate method (Ito et al., 1983) essentially as described (Ausubel et al., *Current Protocols in Molecular Biology*, Greene Publishing Associates and Wiley-Interscience, New York, 1989), and split into six 200 μl aliquots at $2 \times 10^9$ cells/ml. 50 μg of each of the linearized targeting plasmids (in 20 μl) is mixed with 10 μg (2 μl) sonicated calf thymus DNA and added to a 200 μl aliquot of cells. After transformation, cells are spread onto the surface of CM-arg, trp, and uracil agar plates and incubated at 30° C. for 3–5 days. The omission of uracil from the media selects for cells that have stably integrated the targeting plasmid derived from pTKENDC.

C) Analysis of Clones

C.1) Segregation Analysis of Clones

Yeast colonies prototrophic for arginine, tryptophan, and uracil are candidates for clones carrying the targeting plasmid integrated into a human DNA YAC with a region of identity to the targeting sequences on the targeting plasmid. Colonies in which the targeting plasmid integrated into a YAC are identified by a marker segregation assay. The loss patterns of the three markers are analyzed in cells derived from the selected clone which have lost the YAC after growth on non-selective media. Cells are patched onto YPD plates and grown non-selectively for two days, replica plated onto a second YPD plate and grown for another two days. Cells from the second YPD plate are struck-out for single colonies on a third YPD plate. After three days, the plate with single colonies is replica printed onto a CM-arginine, tryptophan plate, and a CM-uracil plate. Clones in which the targeting plasmid is integrated into a YAC are identified by their characteristic pattern of co-loss of all three markers. In these cases all colonies that are auxotrophic for arginine and tryptophan (colonies that lost the markers identifying the YAC) are also auxotrophic for uracil.

C.2) Restriction Enzyme and Southern Blot Analysis of Clones

Total DNA is prepared from yeast colonies prototrophic for arginine, tryptophan, and uracil. The DNA is digested with the same restriction enzyme used to generate the double-strand break in the targeting sequence. 1 μg of the digested DNA is subject to agarose gel electrophoresis and Southern transfer and probed with 32-P labeled DNA corresponding to the fragment of the URA3 gene carried in pTK-ENDC. As a control, 1 ng of the digested plasmid generated in B.1) above is run alongside the yeast DNA samples. A correctly targeted event is characterized by a band on the autoradiograph that migrates exactly the same distance as the pure, linearized targeting plasmid.

C.3) Rescue of Clone Termini to Generate Labeled Probes, Southern Blot Analysis to Identify Sequences that are Single Copy in the Genome Under Analysis, Determination of the Orientation of Cloned Inserts Relative to Vector Arms, Generation of a Targeting Vector from Clone Termini, and Transformation Into Pooled Library 2

The YAC cloning vectors pTKENDA2, pTKENDB, pTKENDC, and pTKENDD have been designed specifically to facilitate the rescue of cloned DNA from the ends of DNA YACs by simple microbiological techniques. One or more recognition sites for restriction enzymes that cut mammalian DNA relatively frequently (approximately once every 0.5–1.5 kb) are positioned at the junction between the bacterial plasmid replicon and the yeast telomere (TEL) or yeast replication origin (ARS) and centromere (CEN) sequences. For any one of the four ends, recognition sites for a subset of such enzymes are not found at any other position in the plasmid replicon or the yeast selectable marker on that end, such that cleavage of total yeast DNA isolated from cells carrying a particular DNA YAC with one of these enzymes rescues (as illustrated in step 3 of FIG. 4) DNA from the cloned insert covalently linked to the yeast selectable marker and bacterial replicon, but free of yeast chromosome replication and stability elements (telomeres, centromeres, and yeast replication origins). This "rescued" DNA is used as the targeting plasmid for the second DNA YAC library. Column 2 of the Table (RESCUE SITES) lists the restriction enzymes useful for rescuing cloned DNA adjacent to each of the four ends in the two DNA YAC libraries. Column 3 (ADDITIONAL ENZYMES) lists some of the additional enzymes that can be used in conjunction with the enzymes listed under RESCUE SITES in the event that a RESCUE SITE enzyme rescues a very long sequence containing a repetitive DNA element that might prevent the clone from being useful for selecting DNA YACs by homologous recombination.

TABLE

| YAC END | RESCUE SITES | | ADDITIONAL ENZYMES | |
|---|---|---|---|---|
| pTKENDA2 | HincII | (1433) | PstI | (3169) |
| | HindIII | (1844) | XhoI | (21462) |
| | SphI | (4522) | EcoRI | (2669) |
| | | | BamHI | (5604) |
| | | | KpnI | (8902) |
| | | | StuI | (3872) |
| | | | AvaII | (790) |
| | | | HpaI | (4240) |
| pTKENDB | HincII | (1433) | XhoI | (21462) |
| | EcoRI | (2669) | TthIII1 | (1070) |
| | | | StyI | (785) |
| | | | BamH | (5604) |
| | | | KpnI | (8902) |
| | | | StuI | (3872) |
| | | | HpaI | (4240) |
| pTKENDC | AhaIII | (1192) | TthIII1 | (1070) |
| | BstYI | (930) | XhoI | (21462) |
| | EcoRI | (2669) | BamHI | (5604) |
| | | | KpnI | (8902) |
| | | | HpaI | (4240) |
| pTKENDD | AhaIII | (1192) | HgiAI | (1348) |
| | BstYI | (930) | HpaI | (4240) |
| | BamHI | (5604) | SphI | (4522) |

The numbers in parentheses represent the average number of base pairs between restriction sites calculated for mammalian DNA.

The recovery, analysis and use of clone termini for recombination walking is illustrated in Steps 3–6 of FIG. 4, U: yeast URA3 gene; X: restriction enzyme cleavage site used to make targeting break; striped box: targeting sequence; thick lines: plasmid sequences for propagation and selection in *E. coli;* Ap: ampicillin resistance gene; Cm: chloramphenicol resistance gene; T: yeast TRP1 gene; A: yeast ARG4 gene; solid circles and horizontal arrowheads: yeast centromere/replication origins and telomeres, respectively; thin lines: cloned human DNA in Library 1; Y: restriction enzyme cleavage sites used for end-rescue; L: yeast LEU2 gene; Km: Kanamycin resistance gene; Tc: tetracycline resistance gene; Z: restriction enzyme cleavage site used to make targeting break in end-rescued DNA; thick shaded line: cloned human DNA in Library 2. The thin line in Library 2 DNA represents a sequence homologous to end-rescued DNA from Library 1.

The remainder of the discussion will relate to isolating (rescuing) the left-hand end of the YAC, but the principles can be extrapolated for homologous recombination walking using any of the four ends in the two DNA Libraries. The vertical arrows marked "Y" can represent the positions of HincII sites lying at various positions throughout the human DNA (for mammalian genomes, HincII sites have an expected distribution of 1 site/1.4 kilobases). The vertical arrow on the extreme left side indicates the position of a HincII site that separates the TEL element from the TRP1-pBSΔ element. Cleavage of total DNA from the yeast strain carrying the YAC illustrated will release the TRP1-pBSΔ fragment from the TEL sequence on the left side, but the right side will remain attached to a fragment of cloned DNA extending to the first HincII site within the insert. The total DNA is ligated under conditions which promote circularization of fragments. A fraction of this DNA is used to transform bacterial cells to isolate ampicillin resistant plasmids.

Approximately 60 μg of plasmid DNA is purified, and several micrograms are digested with HincII and the enzyme used to digest the genomic DNA constituting the library (SnaBI, ApaI, or NsiI). If Library 1 was constructed by cleaving genomic DNA with SmaI and ligated to the SnaBI digested pTKENDB, then an enzyme other than SmaI or SnaBI which flanks the cloning site must be used (for example, ApaI or NsiI). The digest is fractionated on an agarose gel and the non-YAC vector fragment (the rescued insert) is purified and a fraction is labeled with $^{32}$-phosphorus or chromogenic nucleoside triphosphates. This DNA is used in three different ways:

1. The DNA is cut with a selection of restriction enzymes that are known not to cut within the TRP1 pBSΔ sequence. (ADDITIONAL ENZYMES in the Table among others can be used). The digestion products are analyzed by gel electrophoresis to identify restriction enzymes which will cut the cloned DNA isolated from the end of the YAC.
2. The labeled DNA is used to probe a Southern blot filter of human and yeast DNA to determine if the end of the YAC corresponds to a single copy sequence in the human genome, or if it is homologous to the yeast genome. Human sequences that are single copy or low copy and not homologous to yeast DNA are preferred for targeting.
3. The labeled DNA is used to probe a dot-blot, in which total DNA from yeast cells carrying YACs have been isolated and fixed to a Nylon membrane. The membrane is spotted with DNA from the YAC that the labeled DNA is derived from (YAC-Z), the YAC overlapping with YAC-Z which is used to isolate YAC-Z in the previous recombination selection step (YAC-Y), and the YAC overlapping with YAC-Y which was used to isolate YAC-Y in the previous recombination selection step (YAC-X) [i.e., the last three YACs isolated in the walk]. Hybridization only to the YAC from which is derived (YAC-Z in this case) indicates that the TRP1-pBSΔ end of YAC-Z extends in the correct direction, away from the YACs Y and X. This is confirmed by a similar analysis with the other end of YAC-Z, which must hybridize with YAC-Z and YAC-Y and/or YAC-X.

A targeting plasmid meeting the criteria outlined in 2) and 3) above is cleaved with an appropriate restriction enzyme (identified from 1 above) and as denoted as Z in FIG. 4), and used as the targeting plasmid to isolate clones from Library 2, as described in Section B.2 above.

EXAMPLE IV

Methods for Preventing the Occurrence of Repetitive Interspersed DNA at DNA Clone Termini The vectors described in Example III incorporate novel features that are specifically designed to facilitate chromosome walking. First, the two ends of the artificial chromosome are derived from two different plasmids, each with its own sequence to seed telomere formation in yeast, a bacterial origin of replication, a gene for resistance to an antibiotic for selection in *E. coli,* and a selectable gene for clone selection in yeast. This system allows either end of the YAC to be isolated as a bacterial plasmid for amplification and use in each walking step, as opposed to the possibility of isolating only one end with existing YAC vectors.

In the preferred embodiment of any walking strategy, the extreme end of a clone is used as a probe to isolate overlapping clones in the walk. The usefulness of such a probe is limited by the presence of repetitive DNA which may be homologous to thousands of clones within the library. Members of the class of DNA sequences termed highly repetitive interspersed are found at thousands of discreet locations throughout the human genome. Specifically, a member of the Alu family of repetitive DNA sequences is found, on average, spaced at 1 to 3 kilobase intervals throughout the genome (Moyzis, R. K., et al., *Genomics,* 4:273–288, 1989).

The methods and vectors described in Example III have been designed to minimize the occurrence of repetitive DNA at the terminus of the DNA clone inserts in a human DNA YAC vector library. The first feature incorporated into the vector library design is the use of a specific set of restriction endonucleases to cleave human DNA. Numerous DNA sequences from the Alu and L1 family of repetitive DNA were analyzed using computer programs that identify recognition sites for restriction endonucleases. The results of this analysis revealed that recognition sites for the restriction enzymes ApaI, NsiI, and ScaI are not found in the published consensus sequences for any of the Alu subfamilies, and are found only rarely in sequenced members of the L1 family (of approximately 30,000 base pairs of sequences L1 DNA analyzed, there were only five sites for the three enzymes listed above; 23 sites would be expected based on the dinucleotide frequencies found for human DNA). These two families alone account for approximately 10% of the mass of the human genome, indicating that as many as one in ten clone ends (1 in 5 clones) may terminate within one of these repetitive sequences. By using the enzymes disclosed above to cleave human DNA, one creates an inherent bias against the occurrence of these two repetitive sequences at the ends of clones.

The second feature incorporated into the design of the YAC cloning vectors to minimize the occurrence of repetitive DNA in targeting probes used for walking is limiting the size of the DNA probe fragment rescued from the DNA clone end. Smaller DNA fragments have a lower probability of containing repetitive DNA. The vectors described in Example III have been designed to rescue fragments of human DNA on the order of 1–2 kb in length by a single restriction enzyme cleavage of the YAC clone. This is accomplished by the insertion of a polylinker carrying recognition sites for multiple restriction enzymes which cut, on the average, once every 0.5–1.5 kb. When total DNA from yeast carrying the YAC is cut with one of these enzymes, a fragment of DNA containing a plasmid origin of replication and a drug resistance marker (for propagation and selection in *E. coli*), as well as a gene for selection in yeast, and approximately 1–2 kb of human DNA will be released. This fragment can be circularized and transformed into bacteria. As expected, the recognition sites for enzymes that are most useful for this step are found within several of the elements used in the construction of the proposed YAC cloning vectors. In vitro mutagenesis to delete restriction enzyme cleavage sites, along with the judicious choice of combinations for the two plasmid replication origins, the four drug-resistance markers, and the four yeast selectable markers is used to create vectors lacking the frequent-cutting restriction enzyme cleavage sites listed in the Table (Rescue Sites).

EXAMPLE V

Use of Terminal Fragments Derived from Yeast Artificial Chromosome Clones for the Isolation of Clones Known to be Present in a Yeast Artificial Chromosome Library—A Model System to Test the Feasibility of Library Screening Homologous Recombination We used homologous recombination screening to extract a clone from the library that was known to exist within the library. Since the vector arm containing the TRP1 gene in YACs constructed with pYAC4 contains a plasmid replicon and a selectable marker (the beta-lactamase gene conferring ampicillin resistance), the technique of "plasmid rescue" was used to isolate terminal fragments from two YACs constructed in the vector pYAC4. The restriction enzyme XhoI cleaves at a single site within the TRP1 vector arm, at the junction between the telomere and pBR322 sequences. Complete digestion of YAC DNA with XhoI should produce a restriction fragment devoid of telomeric sequences, containing a functional plasmid replicon and Amp$^r$ marker, and harboring a segment of human DNA that was adjacent to the vector arm in the original YAC clone and extends to the terminal XhoI site in the human DNA insert.

A group of 161 YACs within the library were constructed using the host yeast strain MGD131-10c (genotype a leu2-3,112 ADE2 cyh2$^r$ hisΔ1 trp1-289 agr4Δ ura3-52). Total DNA from two clones in this group was digested with XhoI, ligated under dilute conditions to promote intramolecular circularization, and transformed into *E. coli* (all steps carried out essentially as described in Ausubel et al., 1988 [above]). Plasmid DNA was isolated from ampicillin resistant colonies and subjected to restriction enzyme analysis. One human DNA fragment from each of the two rescued plasmids was subsequently blunt-ended by treatment with T4 polymerase and ligated into the SmaI site of p184DLARG. The fragments, 10B and 8A, are 1 and 4 kb fragments, respectively, of human DNA lying adjacent to the TRP1 vector arms in two different YACs. The resulting constructs (plasmids p184-10B and p184-8A) were digested with a number of restriction enzymes which do not cleave p184DLARG to identify an enzyme that would cut within the human DNA to promote targeting. 20 μg of each construct was digested with the appropriate targeting enzyme and used for library screening, essentially as described in Example 1. Fragment 8A contains a single Kpn1 site lying 2–8 Kb from one end and this enzyme was used to introduce a unique double strand break within the inserted sequence in p184-8A. Fragment 10B contains a single AvaII site lying 0.5 Kb from one end and this enzyme was used to introduce a unique double strand break within the inserted sequence in p184-10B.

Eleven arg$^+$ colonies resulting from screening with clone 8A were isolated and analyzed. Similar to strain IV-16d (Example 1 and ATCC Accession No. 74010) strain MGD131-10c carries a 2 kb deletion encompassing the entire ARG4 gene. However, the two strains differ with regard to their LEU2 genotype; IV-16d is leu$^+$ and MGD131-10c has a leu$^-$ phenotype. Seven of the eleven colonies displayed a leu$^-$ phenotype, suggesting that they indeed represented independent isolates of the original YAC from which clone 8A was derived (a very strong possibility since strain MGD131-10c was the host for only 161 out of the 11,625 YACs (1.4%) in the library). Seventeen arg$^+$ colonies resulting from screening with clone 10B were isolated and analyzed. Three of the 17 colonies displayed the leu$^-$ phenotype. The presence of the leu$^-$ marker strongly suggests that these clones represent isolates of the original YAC from which clone 10B was derived.

Figure 9:
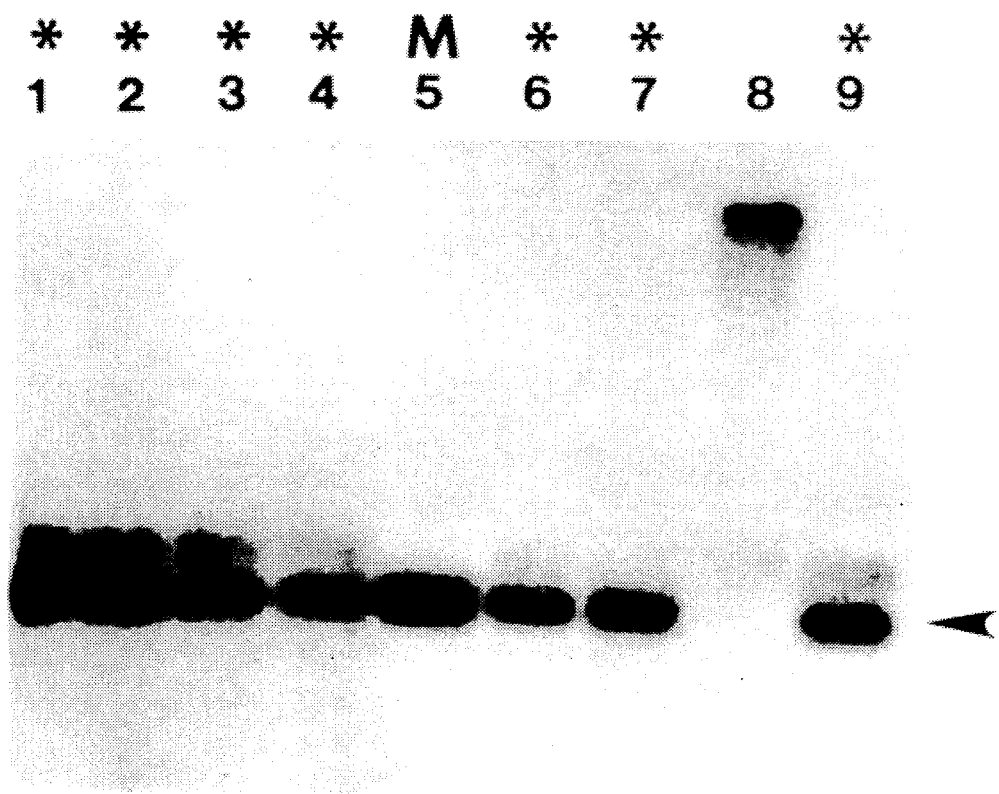
FIG. 9 is photograph of a restriction enzyme and Southern hybridization analysis of DNA from eight yeast colonies isolated by screening with fragment 8A. Lanes 1–4: clones 8A.1, 8A.2, 8A.3 and 8A.4; Lane 5: plasmid p184-8A. Lanes 6–7: clones 8A.5 and 8A.6; Lane 8: an example of DNA from an isolated colony which does not show the unit-length-linear band; Lane 9: clone 8A.11. 1 microgram of total yeast DNA was loaded in lanes 1–4 and 5–9. 2 nanograms of plasmid p184-8A was loaded in lane 5. The electrophoresed DNA samples (all digested with KpnI) were transferred to a nylon membrane and hybridized with a 32-P labeled ARG4 DNA probe. The arrow marks the position of the unit-length-linear band at 8.3 kb.

DNA was prepared from each of the seven leu$^-$ colonies isolated by screening with clone 8A as well as one of the leu$^+$ colonies. DNA was digested with the same enzyme used to linearize the transforming DNA molecule (KpnI). A Southern blot of these digests were probed with 32-P labeled ARG4 DNA. As described in Example 1, homologous integration events should reveal hybridization to a single fragment of exactly the same size as the linearized transforming DNA molecule (referred to in Example 1 as a Unit Length Linear Fragment, or ULL). Of the eight clones analyzed, all seven in strain MGD131-10c (the leu$^-$ colonies) represent homologous events, while the single leu$^+$ transformant analyzed (lane 8) does not (FIG. 9). Thus, seven out of eleven candidate clones isolated were correctly targeted events. A similar analysis was performed on each of the three leu$^-$ colonies isolated by screening with clone 10B. All three clones displayed a ULL upon Southern blot analysis, while 14 leu$^+$ transformants did not.

Figure 10:
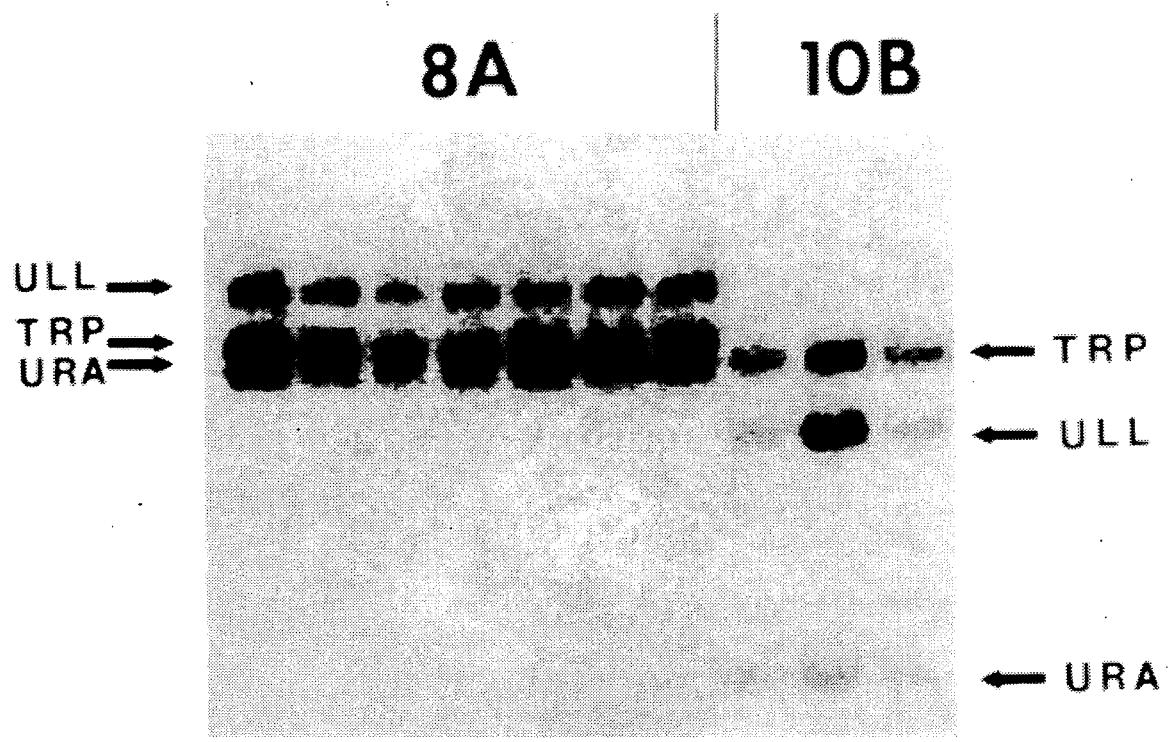
FIG. 10 is a photograph of a restriction enzyme and Southern hybridization analysis of DNA from each of the positive clones digested with XhoI and with either KpnI (for those isolated by screening with fragment 8A) or AvaII (for those isolated by screening with fragment 10B). Samples were electrophoresed on a 1% agarose gel, transferred to a nylon filter, and hybridized with $^{32}P$ labeled pBR328 (Boehringer Mannheim Biochemicals, Indianapolis, Ind.). Lanes 1–7: clones 8A.1, 8A.2, 8A.3, 8A.4, 8A.5, 8A.6, 8A.11 (all isolated by screening with fragment 8A); lanes 8–10: clones 10B.6, 10B.29, 10B.41 (isolated by screening with fragment 10B).

To confirm that the three homologous events isolated by screening with clone 10B and the seven homologous events isolated by screening with clone 8A represent the independent isolates of the same YACs, we have mapped the termini of the YACs in these ten clones. FIG. 10 shows the result of this analysis. Three bands are evident in each lane, corresponding to the ULL, the left arm, and the right arm of the YAC. The bands migrate at identical positions in all seven YACs isolated with 8A, and at different, but identical positions in all three YACs isolated with 10B. These data show that the distance to the nearest KpnI site at each end of the seven 8A YACs is identical, while the three 10B YACs display similar behavior for the positions of their terminal AvaII sites.

EXAMPLE VI

Screening of a Human Yeast Artificial Chromosome Library by Homologous Recombination to Isolate a Yeast Artificial Chromosome Clone Derived from the Human Adenosine Deaminase Locus Synthetic oligonucleotides o6 and o7-2 were used in the polymerase chain reaction to amplify a 1,376 base pair fragment of the human ADA gene corresponding to positions 34,243–35,618 (Genbank Entry HUMADAG) from total human genomic DNA isolated from peripheral blood leukocytes. The amplified fragment was digested with PstI and the 852 base pair subfragment corresponding to HUMADAG positions 34,349–35,201 was isolated and cloned into the PstI site of plasmid p184DLARG (Example 1). One insert orientation was chosen (that with HUMADAG 34,349 position adjacent to the 3' end of the yeast ARG4 gene in p184DLARG. The resulting plasmid was purified and 20 micrograms was linearized at the unique EcoNI site within the human ADA insert (corresponding to HUMADAG position 34,657) prior to transformation into the pooled YAC library. Transformation of the pooled YAC library was performed exactly as described in Example 1, with the exception being that the YAC library consisted of an additional 3,585 clones, for a total of 15,210 clones representing approximately 1.2 genome equivalents.

Figure 11:
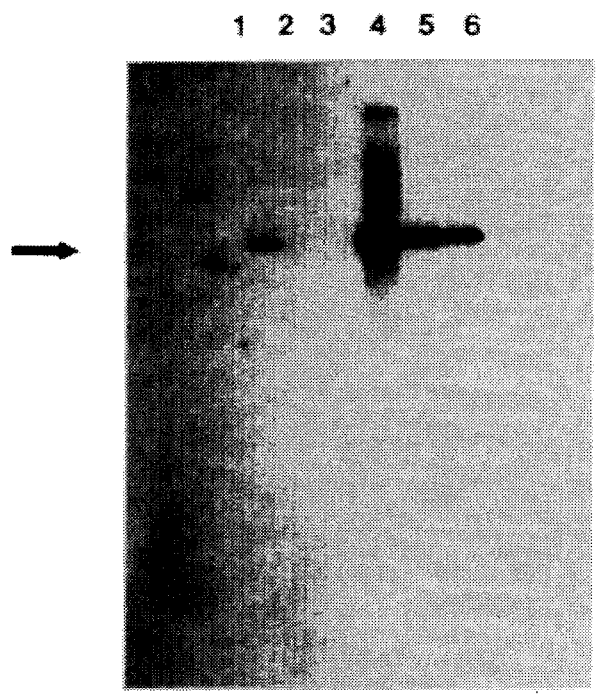
FIG. 11 shows analysis of YAC DNA for presence of unit-length-linear fragments hybridizing to an ARG4 DNA probe: Lane 1: EcoNI digest of plasmid p184DLARG/PCRF.5, which contains the 852 base pair PstI fragment from the human ADA locus cloned into the PstI site of p184DLARG. 1 nanogram of digested plasmid DNA was loaded; Lanes 2–3: empty (no samples loaded); Lanes 3–6: EcoNI digested YAC DNA (approximately 1 microgram) from candidate transformants 184ADA.B, 184ADA.C, and 184ADA.D. The electrophoresed samples were transferred to a nylon membrane and hybridized to a 32-P labeled fragment of ARG4 DNA. The arrow indicates the position of EcoNI linearized plasmid p184DLARG/PCRF.5 (5.2 kb).

Four arg$^+$ transformants were isolated. Three of these are displayed in FIG. 11 and all three displayed a unit-length linear fragment upon restriction enzyme digestion with EcoNI and Southern blot analysis. Analysis of the fourth arg$^+$ transformant confirmed that it carries the same insert as YAC 184ADA.C and 184ADA.D. All four transformants harbor a similarly sized YAC of ca. 200 kb, as judged by CHEF gel electrophoresis. The intensity of the ULL band in DNA prepared from YAC 184ADA.B and other data indicate that YAC 184ADA.B has undergone multiple tandem integrations of the targeting plasmid.

Comparison of a representative YAC, YAC 184ADA.C, with human genomic DNA by restriction enzyme and Southern hybridization analysis using multiple probes and restriction digests confirmed that this YAC indeed contains sequences from the human ADA locus.

OLIGONUCLEOTIDE o6

5' AGATCTGTTT$^{10}$ GAGGCTGCTG$^{20}$ TGAG SEQ ID NO: 29

Bases numbered 1–24 corresponding to positions 34,243–34,266 in GENBANK Entry HUMADAG.

OLIGONUCLEOTIDE o7-2

5' AGATCCGGCA$^{10}$ ACTTGTAGTA$^{20}$ CCCAGGATG SEQ ID NO.:30

Bases numbered 7–29 corresponding to positions 35,618–35,596 in GENBANK Entry HUMADAG. Bases 1–6 corresponding to one of the four possible recognition sequences for the restriction enzyme BstYI, added to facilitate cloning.

EXAMPLE VII

Quantification of Effect of Chromosomal Deletions of Homologous Sequences Present in Host Cell Orr-Weaver et al. (*Proc. Natl. Acad. Sci. U.S.A.*, Vol. 78, 10:6354–6358, October 1981) showed that a plasmid carrying the yeast LEU2 gene results in leu$^+$ transformants at a frequency of 1.4–1.7 per µg of DNA when a double-strand break was made in the pBR322 portion of the plasmid. This is 1/10 of the frequency at which leu$^+$ transformants arose when targeting was directed to the LEU2 gene by a double-strand break in LEU2 sequences (12–17 per µg DNA). Similarly, when a HIS3 containing plasmid was cut within pBR322 sequences, his$^+$ transformants appeared at 1/60 of the rate observed when the same plasmid was cut within HIS3. In both cases, the non-targeted prototrophs were demonstrated to be the results of recombination between the plasmid and the chromosomal leu2$^-$ and his3$^-$ mutant genes. Thus, screening a library for one clone out of 50,000 by homologous recombination without deletion of the chromosomal LEU2 gene would be expected to yield 5,000 leu$^+$ transformants which arise through homologous recombination with the yeast genome when the targeting plasmid carries LEU2, even if a double-strand targeting break is made in another part of the plasmid. The results suggest, however, that deleting the chromosomal copies of LEU2 and HIS3 would eliminate virtually all of the nontargeted events.

The advantage of chromosomal deletions from host cells for the purposes of the method was quantified as follows: A plasmid carrying the yeast ARG4 ("target") and URA3 ("marker") genes was transformed into a mixture of yeast cells after making a double-strand break at the unique BclI site in the ARG4 sequence. All of the cells in the mixture had homology to URA3, but only 1 in 1,000 or 1 in 10,000 had homology to ARG4. This type of dilution experiment measures the relative frequencies of targeted and non-targeted events. For example, using 1 µg of DNA and a 1 to 1,000 dilution, the isolation of 5 yeast colonies by homologous recombination at ARG4 indicates that 5,000 cells were theoretically capable of a targeted event, but only 5/5,000 cells actually had the necessary homology at ARG4. The targeting frequency is therefore equivalent to 5,000 targeted events per µg in an undiluted culture. If, in the same experiment, 5 colonies were isolated that were independent of homology at ARC4 (recombination at URA3 or elsewhere, non-targeted events), the frequency of these non-targeted events is 5 per µg, and the ratio of targeted to non-targeted events in this experiment would be 1,000 to 1.

For the 1 in 1,000 dilution, 78 targeted transformants were isolated (by recombination with ARG4; equivalent to 78,000 targeted events) and 17 by recombination elsewhere (non-targeted events). At a dilution of 1 in 10,000, four targeted events (equivalent to 40,000 targeted events) and seven non-targeted events were isolated. The ratio of targeted to non-targeted events is thus (78,000+40,000) divided by (17+7), or 4,917 to 1. This ratio would lead to approximately 10 incorrect events for every one correct event when screening a library for a sequence present on 1 in 50,000 YACs, which is several-fold too high to be generally acceptable, although the use of URA3 as a targeting marker is clearly preferred over the use of the LEU2 or HIS3 markers previously used in targeting studies (Orr-Weaver et al., 1981). 84% (16 of 19 analyzed) of the non-targeted events where in fact due to recombination between the URA3 marker on the plasmid and the chromosomal ura3$^-$ locus. If there were no homology between the targeting plasmid and the chromosomal ura3$^-$ locus, then the non-targeted events resulting from homology at the ura3$^-$ locus are removed from the analysis and the ratio increases to 30,729 to 1. At this ratio, a sequence represented 3 times in 50,000 YACs would be correctly targeted 1.8 times for every one non-targeted event. This ratio would also result in the favorable ratio of one correct event for every 1.6 incorrect events when screening a library for a sequence present on only 1 in 50,000 YACs.

These results indicate that the selection of a targeted clone from a DNA YAC library is feasible and particularly efficient in host yeast cells that carry no homology with selectable markers present on targeting vectors.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of producing a physical map of contiguous DNA sequences, comprising the steps of:

a) providing a first DNA fragment library and a second DNA fragment library, wherein the first library and the second library are in a population of yeast host cells of the genus Saccharomyces; DNA fragments are present in yeast host cells in an artificial chromosome which is replicated in the yeast host cells and includes 1) two sequences necessary for propagation in bacteria, one at each end of the artificial chromosome 2) two different marker genes for selection in bacteria, one at each end of the artificial chromosome and 3) two different marker genes for selection in yeast, one at each end of the artificial chromosome; and the selectable markers in the first library are not the same as the selectable markers in the second library;

b) introducing into the first DNA fragment library a targeting DNA vector which is non-replicating in the yeast host cells, the targeting vector comprising a marker gene for selection in yeast and targeting DNA which is homologous in part to a target DNA fragment, thereby producing a mixed population of yeast host cells;

c) maintaining the mixed population of yeast host cells of step (b) under conditions appropriate for homologous recombination to occur, whereby yeast host cells containing the target DNA fragment are stably transformed with the marker gene for selection in yeast and targeting DNA present in the targeting vector as a result of homologous recombination between the target DNA fragment and the targeting DNA, and whereby stably transformed yeast host cells with a selectable phenotype and containing the target DNA fragment are produced;

d) selecting stably transformed yeast host cells exhibiting the selectable phenotype;

e) digesting total DNA from stably transformed yeast host cells with a restriction enzyme, thereby releasing from artificial chromosomes an artificial chromosome region which includes a target DNA fragment terminus, a marker gene for selection in bacteria; a marker gene for selection in yeast and sequences necessary for propagation in bacteria, all of which were located at an end of an artificial chromosome, thereby isolating an artificial chromosome region;

f) circularizing the artificial chromosome region produced in the previous step, thereby producing a circularized DNA molecule which is referred to as a subsequent targeting vector and comprises the artificial chromosome region produced in step (e), wherein the target DNA fragment terminis is referred to as a subsequent targeting DNA;

g) selecting and amplifying the subsequent targeting vector in bacteria;

h) introducing into the second DNA fragment library the subsequent targeting vector, thereby producing a mixed population of yeast host cells;

i) maintaining the mixed population of yeast host cells of step (h) under conditions appropriate for homologous recombination to occur, whereby yeast host cells containing the target DNA fragment are stably transformed with the marker gene for selection in yeast and the targeting DNA present in the subsequent targeting vector as a result of homologous recombination between a target DNA fragment and the subsequent targeting DNA, and whereby stably transformed yeast host cells with a selectable phenotype and containing the target DNA fragment are produced;

j) selecting stably transformed yeast host cells which exhibit the selectable phenotype;

k) repeating steps (e) through (j) as needed; and l) constructing a physical map by ordering target DNA fragments obtained.

2. A method of claim 1 wherein the targeting DNA vector is a bacterial plasmid.

3. A method of claim 2 wherein the bacterial plasmid has a double-strand break introduced within the targeting DNA.

4. A method of producing a physical map of contiguous DNA sequences, comprising the steps of:

a) providing a first DNA fragment library and a second DNA fragment library, wherein the first library and the second library are in a population of host cells of the species *Saccharomyces cerevisiae;* DNA fragments are present in host cells in an artificial chromosome which is replicated in the host cells and includes 1) two sequences necessary for propagation in bacteria, one at each end of the artificial chromosome, 2) two different marker genes for selection in bacteria, one at each end of the artificial chromosome, and 3) two different marker genes for selection in the host cells, one at each end of the artificial chromosome; and the selectable markers in the first library are not the same as the selectable markers in the second library;

b) introducing into the first DNA fragment library a targeting DNA vector which is non-replicating in the host cells, the targeting vector comprising a marker gene for selection in the host cells and targeting DNA which is homologous in part to a target DNA fragment, thereby producing a mixed population of host cells;

c) maintaining the mixed population of host cells of step (b) under conditions appropriate for homologous recombination to occur, whereby the host cells containing the target DNA fragment are stably transformed with the marker gene for selection in yeast as a result of homologous recombination between the target DNA fragment and the targeting DNA, and whereby stably transformed host cells with a selectable phenotype and containing the target DNA fragment are produced;

d) selecting stably transformed host cells exhibiting the selectable phenotype;

e) digesting total DNA from stably transformed host cells with a restriction enzyme, thereby releasing from artificial chromosomes an artificial chromosome region which includes a target DNA fragment terminus, a marker gene for selection in bacteria, a marker gene for selection in host cells and sequences necessary for propagation in bacteria, all of which were located at an end of an artificial chromosome, thereby isolating an artificial chromosome region;

f) circularizing the artificial chromosome region produced in the previous step, thereby producing a circularized DNA molecule which is referred to as a subsequent targeting vector and comprises the artificial chromosome region produced in step (e), wherein the target DNA fragment terminus is referred to as a subsequent targeting DNA;

g) selecting and amplifying the subsequent targeting vector in bacteria;

h) introducing into the second DNA fragment library the subsequent targeting vector, thereby producing a mixed population of host cells;

i) maintaining the mixed population of host cells of step (h) under conditions appropriate for homologous recombination to occur, whereby host cells containing the target DNA fragment are stably transformed with the marker gene for selection in host cells and the targeting DNA present in the subsequent targeting vector as a result of homologous recombination between a target DNA fragment and the subsequent targeting DNA, and whereby stably transformed host cells with a selectable phenotype and containing the target DNA fragment are produced;

j) selecting stably transformed host cells which exhibit the selectable phenotype;

k) repeating steps (e) through (j) as needed; and l) constructing a physical map by ordering target DNA fragments obtained.

* * * * *

UNITED STATES PATENT AND TRADEMARK OFFICE
CERTIFICATE OF CORRECTION

PATENT NO. : 5,580,734
DATED : December 3, 1996
INVENTOR(S) : Douglas A. Treco and Allan M. Miller It is certified that error appears in the above-indentified patent and that said Letters Patent is hereby corrected as shown below:

On the title page, in item [54] and col. 1, line 2
    after "Map", delete "Contigous" and insert --of Contiguous--.

Claim 1, column 51, line 24: delete "terminis" and insert --terminus--.

Signed and Sealed this

Twenty-fifth Day of February, 1997

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
    ( A ) LENGTH: 23 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:1:

AATTCAACAA GCAAGTGCGA TGC     23

( 2 ) INFORMATION FOR SEQ ID NO:2:

( i ) SEQUENCE CHARACTERISTICS:
    ( A ) LENGTH: 27 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:2:

CGTTCACGCT ACGTACCCGG GCCCTAG     27

( 2 ) INFORMATION FOR SEQ ID NO:3:

( i ) SEQUENCE CHARACTERISTICS:
    ( A ) LENGTH: 37 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:3:

AATTCAACAA GCAAGTGCGA TGCATGGGCC CGGGATC     37.

( 2 ) INFORMATION FOR SEQ ID NO:4:

( i ) SEQUENCE CHARACTERISTICS:
    ( A ) LENGTH: 37 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:4:

GATCCCGGGC CCATGCATCG CACTTGCTTG TTGAATT     37

( 2 ) INFORMATION FOR SEQ ID NO:5:

( i ) SEQUENCE CHARACTERISTICS:
    ( A ) LENGTH: 41 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:5:

AATTCACATG TGTCAACTAA ACATAAAACT CGAGGGGATC C    41

( 2 ) INFORMATION FOR SEQ ID NO:6:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

GAGCTCCCCT AGGATGCATT ACGTACCCGG GATATTTTCT AG    42

( 2 ) INFORMATION FOR SEQ ID NO:7:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

AATTCACATG TGTCAACTAA ACATAAAACT CGAGGGATC CTACGTAATG CATGGGCCCT    60

ATAAAAGATC    70

( 2 ) INFORMATION FOR SEQ ID NO:8:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

GATCTTTTAT AGGGCCCATG CATTACGTAG GATCCCCTCG AGTTTTATGT TTAGTTGACA    60

CATGTGAATT    70

( 2 ) INFORMATION FOR SEQ ID NO:9:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

AATTCGGATC TTTAAACATA AAAGCTTCCG GATCCCG    37

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

CGAAGGCCTA GGGCCCGGGT ACGTACTAG    29

( 2 ) INFORMATION FOR SEQ ID NO:11:

( i ) SEQUENCE CHARACTERISTICS:
        ( A ) LENGTH: 52 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

AATTCGGATC TTTAAACATA AAAGCTTCCG GATCCCGGGC CCATGCATGA TC    52

( 2 ) INFORMATION FOR SEQ ID NO:12:

( i ) SEQUENCE CHARACTERISTICS:
        ( A ) LENGTH: 52 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

GATCATGCAT GGGCCCGGGA TCCGGAAGCT TTTATGTTTA AAGATCCGAA TT    52

( 2 ) INFORMATION FOR SEQ ID NO:13:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

GATCCTTTAA ACATAAAAGC TTGGAGATCT AG    32

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

GAACCTCTAG ATCATGACCC GGGTACGTAG GATC    34

( 2 ) INFORMATION FOR SEQ ID NO:15:

( i ) SEQUENCE CHARACTERISTICS:
        ( A ) LENGTH: 53 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

GATCCTTTAA ACATAAAAGC TTGGAGATCT AGTACTGGGC CCATGCATCC TAG    53

( 2 ) INFORMATION FOR SEQ ID NO:16:

( i ) SEQUENCE CHARACTERISTICS:

(A) LENGTH: 53 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:16:

CTAGGATGCA TGGGCCCAGT ACTAGATCTC CAAGCTTTTA TGTTTAAAGG ATC        53

(2) INFORMATION FOR SEQ ID NO:17:

(i) SEQUENCE CHARACTERISTICS:
(A) LENGTH: 23 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:17:

GATCTGAGCT CAAGGAACAG CTG        23

(2) INFORMATION FOR SEQ ID NO:18:

(i) SEQUENCE CHARACTERISTICS:
(A) LENGTH: 19 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:18:

ACTCGAGTTC CTTGTCGAC        19

(2) INFORMATION FOR SEQ ID NO:19:

(i) SEQUENCE CHARACTERISTICS:
(A) LENGTH: 23 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:19:

GATCTGAGCT CAAGGAACAG CTG        23

(2) INFORMATION FOR SEQ ID NO:20:

(i) SEQUENCE CHARACTERISTICS:
(A) LENGTH: 19 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:20:

CAGCTGTTCC TTGAGCTCA        19

(2) INFORMATION FOR SEQ ID NO:21:

(i) SEQUENCE CHARACTERISTICS:
(A) LENGTH: 25 base pairs
(B) TYPE: nucleic acid
(C) STRANDEDNESS: single
(D) TOPOLOGY: linear ( i i ) MOLECULE TYPE: DNA (genomic)

( x i ) SEQUENCE DESCRIPTION: SEQ ID NO:21:

GGTCTCTACA GGTTCTGACA TTATT 25

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

CCGGCGTAGA GAATCCACAG GACGG 25

( 2 ) INFORMATION FOR SEQ ID NO:23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

CTCCTGATGA CGCATGGTTA CTC 23

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

GGAAAGAAAT GCACAAGCTT TTGCC 25

( 2 ) INFORMATION FOR SEQ ID NO:25:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CCGATACCAG GACCTTGCCA TCC 23

( 2 ) INFORMATION FOR SEQ ID NO:26:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TAAACATAAA A 11

( 2 ) INFORMATION FOR SEQ ID NO:27:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CGGAATTCCG        10

( 2 ) INFORMATION FOR SEQ ID NO:28:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GCTCTAGAGC        10

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

AGATCTGTTT GAGGCTGCTG TGAG        24

( 2 ) INFORMATION FOR SEQ ID NO:30:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

AGATCCGGCA ACTTGTAGTA CCCAGGATG        29